United States Patent
Hodorek et al.

(10) Patent No.: US 10,856,994 B1
(45) Date of Patent: Dec. 8, 2020

(54) IMPLANTS, SYSTEMS AND METHODS OF USING THE SAME

(71) Applicant: IGNITE ORTHOPEDICS LLC, Warsaw, IN (US)

(72) Inventors: Brian C. Hodorek, Winona Lake, IN (US); Matthew J. Purdy, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US); Luke Austin, Haddonfield, NJ (US)

(73) Assignee: IGNITE ORTHOPEDICS LLC, Warsaw, IN (US)

( * ) Notice: Subject to any disclaimer, the term of this patent is extended or adjusted under 35 U.S.C. 154(b) by 0 days.

(21) Appl. No.: 16/947,640

(22) Filed: Aug. 11, 2020

Related U.S. Application Data

(63) Continuation of application No. 16/799,501, filed on Feb. 24, 2020, now Pat. No. 10,736,751, which is a continuation of application No. PCT/US2019/043990, filed on Jul. 29, 2019.

(60) Provisional application No. 62/711,449, filed on Jul. 27, 2018.

(51) Int. Cl.
*A61F 2/40* (2006.01)
*A61F 2/30* (2006.01)
*A61F 2/46* (2006.01)

(52) U.S. Cl.
CPC ........ *A61F 2/4081* (2013.01); *A61F 2/30749* (2013.01); *A61F 2/4612* (2013.01); *A61F 2002/30224* (2013.01); *A61F 2002/30245* (2013.01); *A61F 2002/30433* (2013.01); *A61F 2002/4085* (2013.01)

(58) Field of Classification Search
CPC ........ A61F 2/40; A61F 2/4014; A61F 2/4081; A61F 2002/4037; A61F 2002/30507; A61F 2002/30878; A61F 2002/30884; A61F 2002/30433
See application file for complete search history.

(56) References Cited

U.S. PATENT DOCUMENTS

| | | |
|---|---|---|
| 6,228,120 B1 | 5/2001 | Leonard |
| 6,673,114 B2 | 1/2004 | Hartdegen |
| 6,736,852 B2 | 5/2004 | Callaway |

(Continued)

FOREIGN PATENT DOCUMENTS

| | | |
|---|---|---|
| CN | 203074933 | 7/2013 |
| FR | 2960418 | 12/2011 |

(Continued)

OTHER PUBLICATIONS

International Search Report and Written Opinion of the International Searching Authority for PCT/US2019/043990, dated Oct. 28, 2019, 17 pages.

*Primary Examiner* — Brian A Dukert
(74) *Attorney, Agent, or Firm* — Heslin Rothenberg Farley & Mesiti P.C.; Jacquelyn A. Graff, Esq.

(57) ABSTRACT

Implants, device, systems and methods for replacing an articulation surface in a joint, for example, a reverse glenoid implant with a baseplate, a central screw, a peripheral screw, a modular taper, and a post. Methods for implanting the glenoid implant are also disclosed.

18 Claims, 25 Drawing Sheets

(56) References Cited

U.S. PATENT DOCUMENTS

| | | |
|---|---|---|
| 6,790,234 B1 | 9/2004 | Frankle |
| 6,942,699 B2 | 9/2005 | Stone |
| 7,241,314 B1 | 7/2007 | Winslow |
| 8,002,838 B2 | 8/2011 | Klotz |
| 8,317,871 B2 | 11/2012 | Stone |
| 9,233,003 B2 | 1/2016 | Roche |
| 9,421,106 B2 | 8/2016 | Splieth |
| 9,629,725 B2 * | 4/2017 | Gargac ................. A61F 2/4081 |
| 9,956,083 B2 | 5/2018 | Humphrey |
| 9,962,266 B2 | 5/2018 | Humphrey |
| 10,226,349 B2 | 3/2019 | Sperling et al. |
| 10,433,969 B2 | 10/2019 | Humphrey |
| 2001/0049561 A1 | 12/2001 | Dews |
| 2002/0156534 A1 | 10/2002 | Grusin |
| 2010/0023068 A1 | 1/2010 | Bouttens |
| 2012/0221111 A1 | 8/2012 | Burkhead, Jr. |
| 2013/0150975 A1 | 6/2013 | Iannotti et al. |
| 2015/0305877 A1 | 10/2015 | Gargac et al. |
| 2017/0273806 A1 | 9/2017 | Cardon et al. |
| 2018/0092760 A1 | 4/2018 | Sperling et al. |
| 2018/0280152 A1 | 10/2018 | Mutchler et al. |

FOREIGN PATENT DOCUMENTS

| | | |
|---|---|---|
| WO | 2017007565 | 1/2017 |
| WO | 2018039493 | 3/2018 |

\* cited by examiner

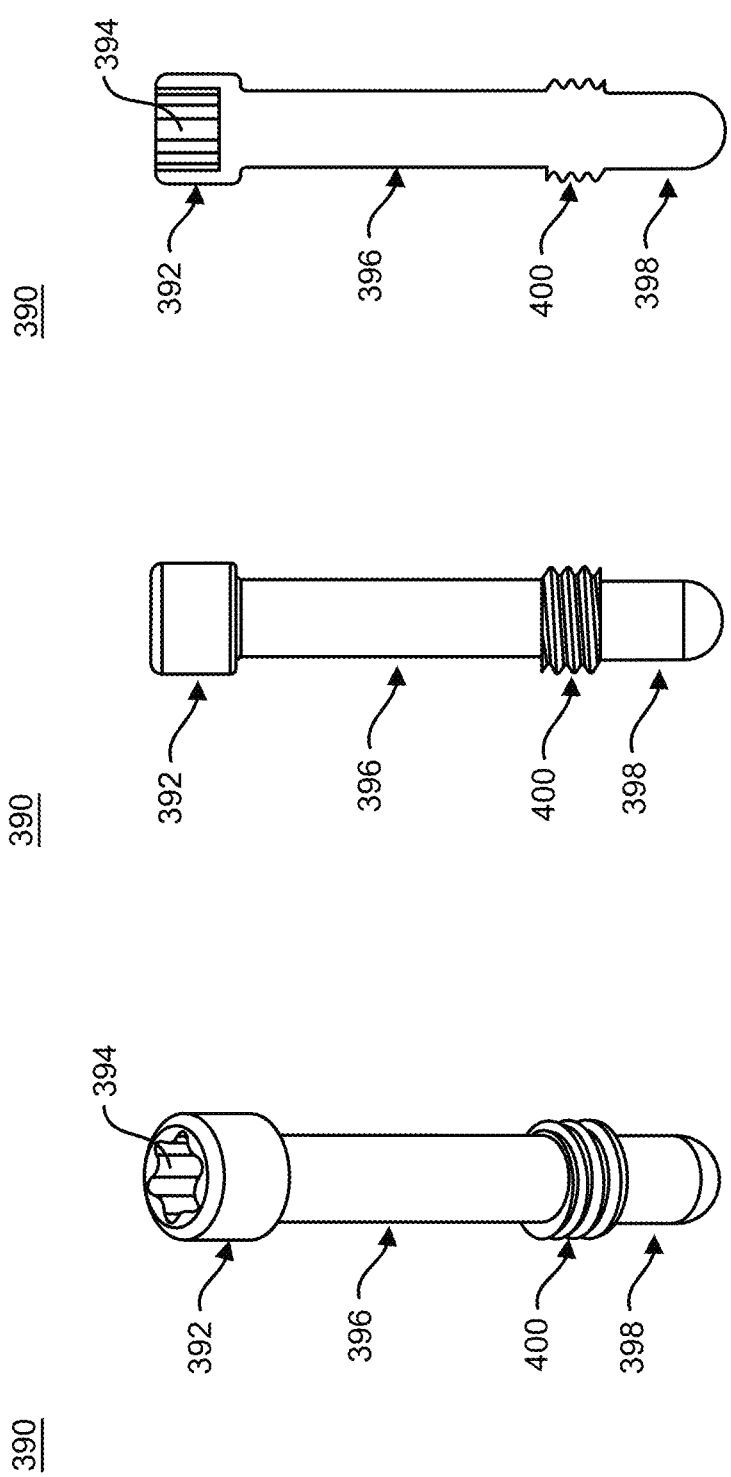

IMPLANTS, SYSTEMS AND METHODS OF USING THE SAME

CROSS-REFERENCE TO RELATED APPLICATION

This application is a continuation of U.S. patent application Ser. No. 16/799,501 filed Feb. 24, 2020 and entitled Implants, Systems and Methods of Using Same, and issuing as U.S. Pat. No. 10,736,751 on Aug. 11, 2020, which is a continuation of PCT/US2019/043990 filed on Jul. 29, 2019 and entitled Implants, Systems and Methods of Using Same, which claims priority benefit under 35 U.S.C. § 119(e) of U.S. provisional application No. 62/711,449 filed Jul. 27, 2018, which are incorporated herein by reference in their entireties.

FIELD OF THE INVENTION

The present invention relates generally to general surgery, orthopedic implants used for replacing an articulation surface in a joint, such as shoulder prostheses. More specifically, but not exclusively, the present invention relates to glenoid implants for reverse shoulder arthroplasties, as well as methods for using the same.

BACKGROUND OF THE INVENTION

Shoulder replacement is a surgical procedure in which all or part of the glenohumeral joint is replaced by a prosthetic implant. Such joint replacement surgery generally is conducted to relieve arthritis pain or fix severe physical joint damage.

Shoulder replacement surgery is an option for treatment of severe arthritis of the shoulder joint. Arthritis is a condition that affects the cartilage of the joints. As the cartilage lining wears away, the protective lining between the bones is lost. When this happens, painful bone-on-bone arthritis develops. Severe shoulder arthritis is quite painful, and it can cause restriction of motion. While this may be tolerated with some medications and lifestyle adjustments, there may come a time when surgical treatment is necessary.

There are a few major approaches to access the shoulder joint. The first is the deltopectoral approach, which saves the deltoid, but requires the subscapularis to be cut. The second is the trans deltoid approach, which provides a straight on approach at the glenoid. However, during this approach the deltoid is put at risk for potential damage.

Shoulder replacement, also known as shoulder arthroplasty or glenohumeral arthroplasty, was pioneered by the French surgeon Jules Emile Pean in 1893. His procedure consisted of physically smoothing the shoulder joint and implanting platinum and rubber materials. The next notable case in the evolution of shoulder replacement procedures was in 1955 when Charles Neer conducted the first hemi-arthroplasty, essentially replacing only the humeral head, leaving the natural shoulder socket, or glenoid, intact. This procedure grew exponentially in popularity as time progressed; however, patients often developed cartilage loss on their glenoid surface as well, leading to pain and glenoid erosion. This prompted the development of a procedure to replace not only the humeral component, but the glenoid component as well.

Throughout the development of the procedures, it became well accepted that the rotator cuff muscles were essential to producing the best outcomes in terms of strength, range of motion, and a decrease in pain. In addition to this finding, physical constraints of the normal ball-and-socket anatomy of the shoulder limited most developments in one way or another. For example, a heavily constrained system limited range of motion and the inherent anatomy of the glenoid proved difficult to cement prosthetics and fixate components without fracturing it. These challenges and high rates of failure led to the development of the reverse total shoulder arthroplasty to overcome the limitations imposed by the natural shoulder anatomy.

The 1970s saw an exponential increase in surgical approaches using this methodology, and the number and variation of surgical techniques are many. However, in 1985 Paul Grammont emerged with a superior technique that is the basis for most reverse shoulder replacement procedures today.

In traditional total shoulder arthroplasty, the approach begins with separating the deltoid muscle from the pectoral muscles, facilitating access to the shoulder (glenohumeral) joint through a relatively nerve free passageway. The shoulder joint is initially covered by the rotator cuff muscles (subscapularis, supraspinatus, infraspinatus & teres minor) and the joint capsule (glenohumeral ligaments). Typically, a single rotator cuff muscle is identified and cut to allow direct access to the shoulder joint. As this point, the surgeon can remove the arthritic portions of the joint and then secure the ball and socket prostheses within the joint.

The development of safer, more effective techniques has led to increased use of reverse total shoulder arthroplasty. Reverse total shoulder arthroplasties are typically indicated when the rotator cuff muscles are severely damaged.

Many existing reverse shoulder systems require a baseplate and a glenosphere. These systems generally differ from one another in how the baseplate is fastened to the glenoid cavity and how the glenosphere becomes engaged to the baseplate. In some systems, the baseplate may be fastened to the glenoid cavity of the scapula by a plurality of screws and a glenosphere having a convex joint surface may be screwed into the baseplate using an axial threaded feature and/or taper that is a part of the baseplate. In other systems, the glenosphere may engage the baseplate solely via a taper connection.

In cases where the glenosphere becomes engaged to the baseplate through either a threaded or taper connection, the glenosphere and baseplate may become separated after a certain length of time. This may cause the glenosphere to tilt with respect to the baseplate or in some cases even separate therefrom. In either situation, the baseplate and glenosphere become misaligned.

Some systems include first fastening a central screw to a glenosphere and then guiding the connection between the baseplate and glenosphere via the central screw. Guiding the connection between the baseplate and glenosphere is generally an important consideration due to minimal access and visibility that the surgeon may have during a reverse shoulder procedure. Access to the baseplate is generally narrow making it relatively difficult for the surgeon to have the visibility needed to correctly align the engagement between a baseplate and glenosphere.

What is needed in the art is a shoulder implant that improves upon prior art devices by providing design advantages that result in less bone loss, improved bone graft retention, and greater initial and long-term implant fixation.

SUMMARY OF THE INVENTION

Aspects of the present disclosure provide glenoid implants for anatomic shoulder arthroplasties. The present invention also provides for methods for using the glenoid implants.

In one aspect, provided herein is an implant that includes a baseplate, a central screw extending through a central bore in the baseplate, and a coupling member engaging a portion of the central bore of the baseplate.

In another aspect, provided herein is are surgical methods for inserting the implants.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 43 is a top perspective view of a post for use with the glenoid implant of FIG. 16, in accordance with an aspect of the present disclosure;

FIG. 44 is a side view of the post of FIG. 43, in accordance with an aspect of the present disclosure; and FIG. 45 is a cross-sectional side view of the post of FIG. 43, in accordance with an aspect of the present disclosure.

DETAILED DESCRIPTION FOR CARRYING OUT THE INVENTION

Figure 1:
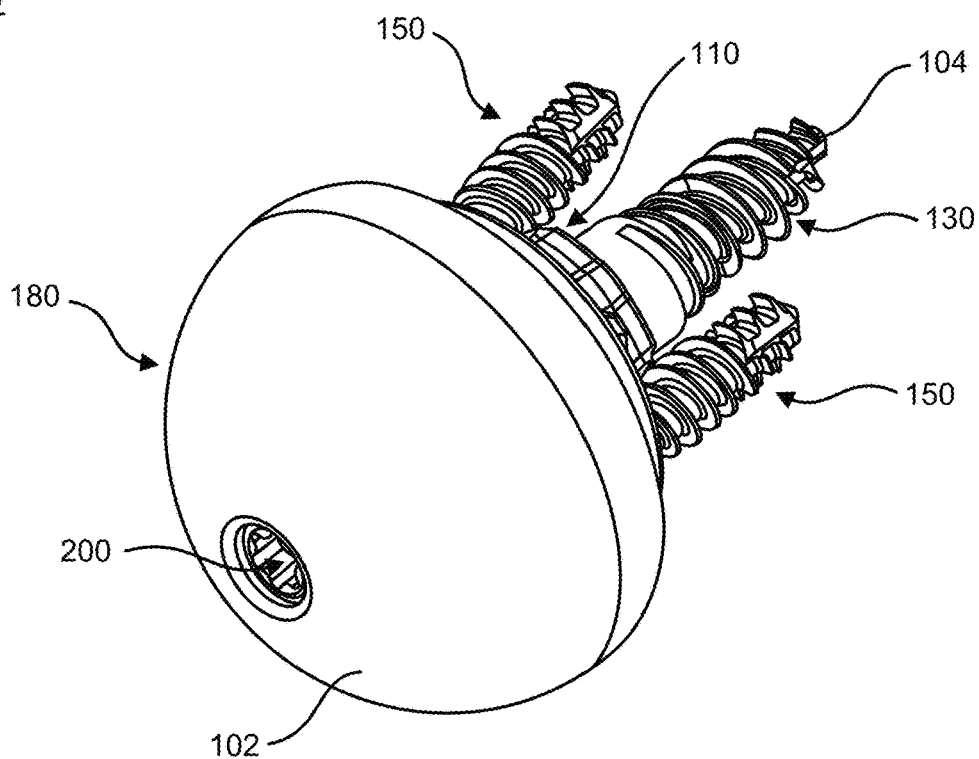
FIG. 1 is a first perspective view of an embodiment of a glenoid implant, in accordance with an aspect of the present disclosure.
Figure 2:
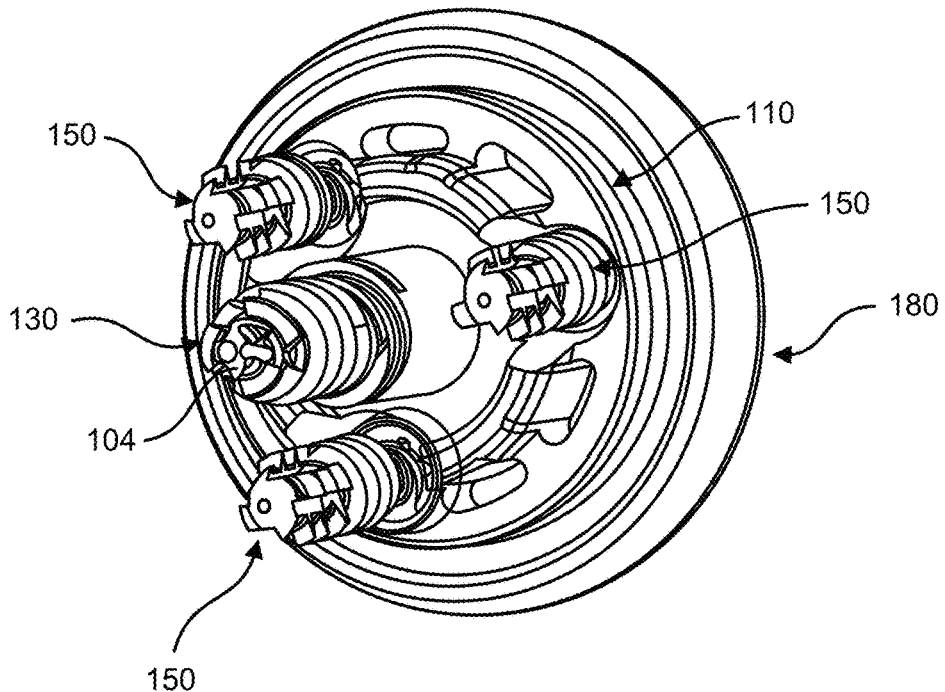
FIG. 2 is a second perspective view of the glenoid implant of FIG. 1, in accordance with an aspect of the present disclosure.
Figure 3:
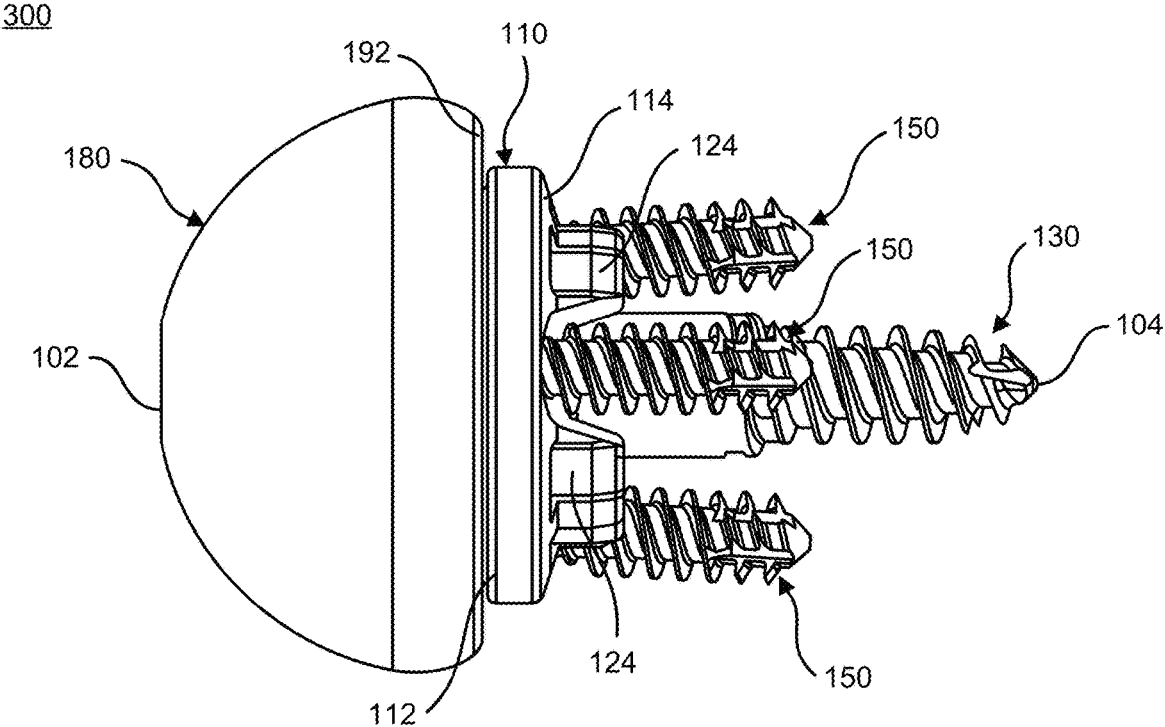
FIG. 3 is a first side view of the glenoid implant of FIG. 1, in accordance with an aspect of the present disclosure.
Figure 4:
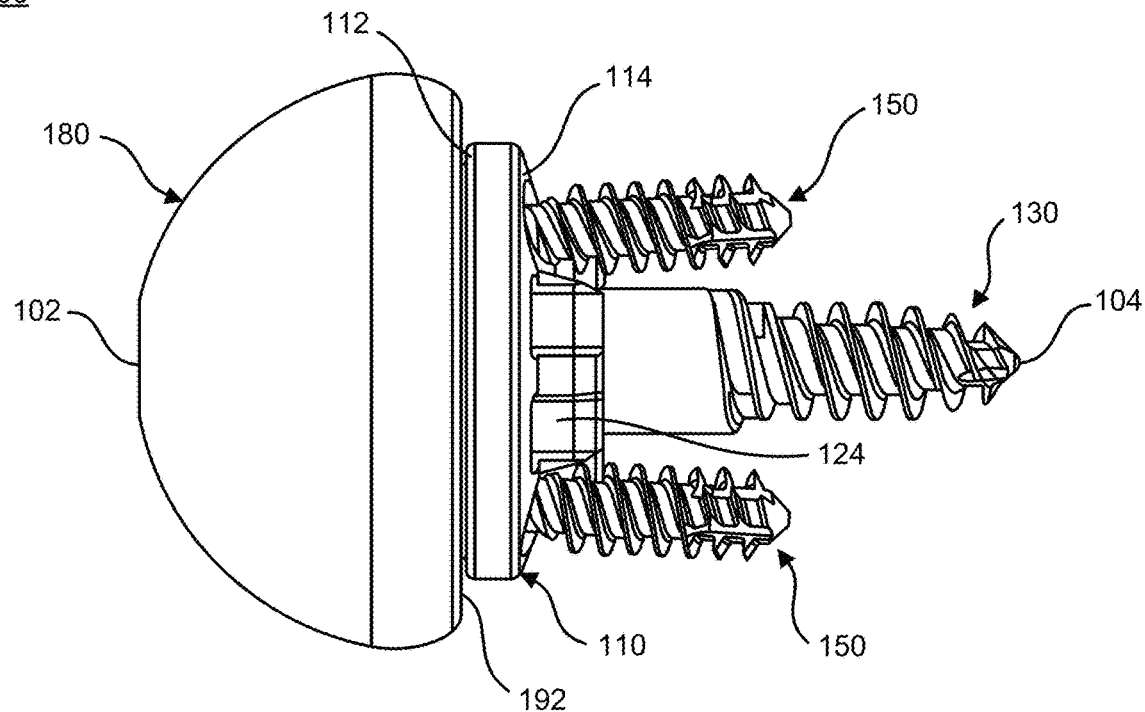
FIG. 4 is a second side view of the glenoid implant of FIG. 1, in accordance with an aspect of the present disclosure.
Figure 5:
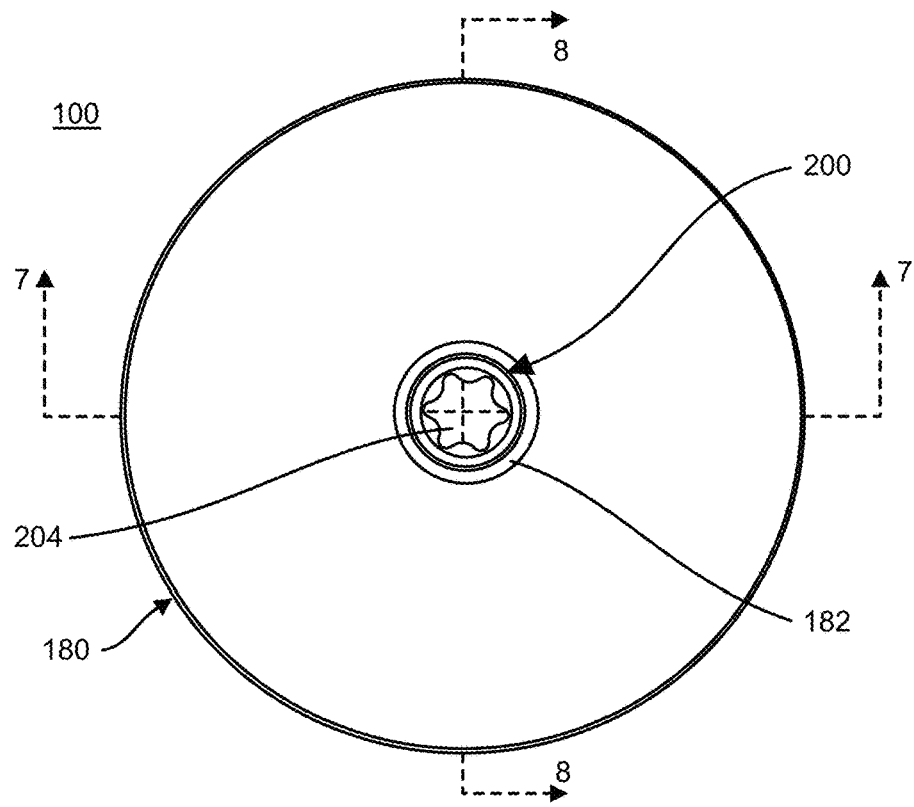
FIG. 5 is a top view of the glenoid implant of FIG. 1, in accordance with an aspect of the present disclosure.
Figure 6:
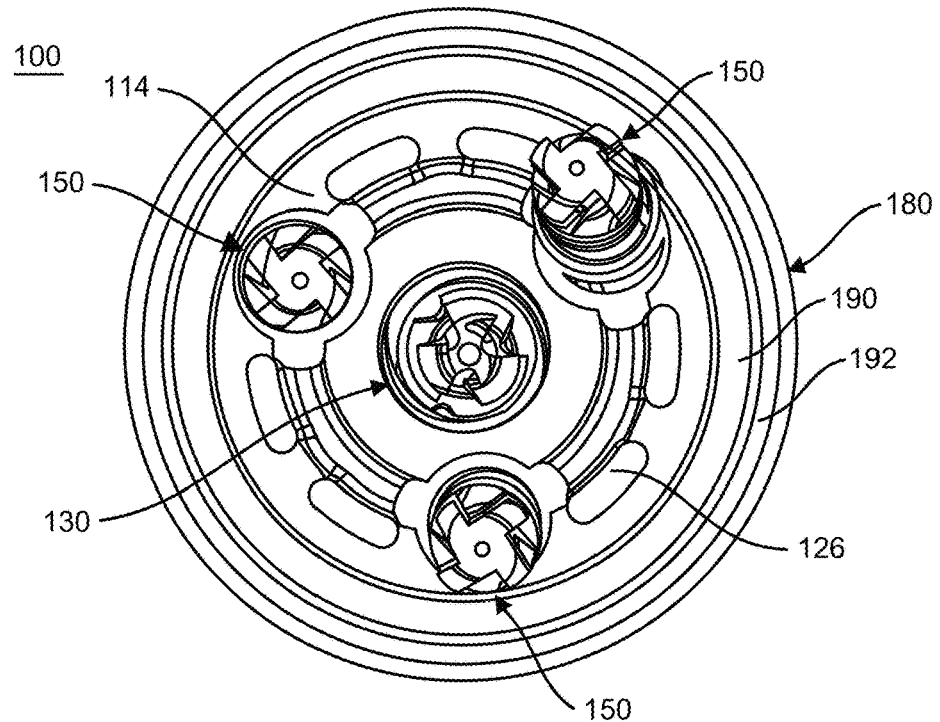
FIG. 6 is a bottom view of the glenoid implant of FIG. 1, in accordance with an aspect of the present disclosure.

Generally stated, disclosed herein are glenoid implants for shoulder prostheses. Further, surgical methods for using the glenoid implants are discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in the first figure of each embodiment.

Similarly, positions or directions may be used herein with reference to anatomical structures or surfaces. For example, as the current implants, devices, systems and methods are described herein with reference to use with the bones of the shoulder, the bones of the shoulder and upper arm may be used to describe the surfaces, positions, directions or orientations of the implants, devices, systems and methods. Further, the implants, devices, systems and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, systems and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, systems and methods, and the aspects, components, features and the like thereof, described herein with respect to the right shoulder may be mirrored so that they likewise function with the left shoulder and vice versa. Further, the implants, devices, systems and methods, and the aspects, components, features and the like thereof, disclosed herein are described with respect to the shoulder for brevity purposes, but it should be understood that the implants, devices, systems and methods may be used with other bones of the body having similar structures, for example the lower extremity, and more specifically, with the bones of the ankle, foot, and leg.

Referring to the drawings, wherein like reference numerals are used to indicate like or analogous components throughout the several views, and with particular reference to FIGS. 1-15, there is illustrated an embodiment of a glenoid implant or reverse glenoid implant 100. The glenoid implant 100 includes a first end or lateral end 102 and a second end or medial end 104. The first end 102 is positioned opposite the second end 104. The glenoid implant 100 also includes a baseplate 110, a central screw 130, at least one peripheral screw 150, a coupling member 160, a glenosphere 180, and a post 200. The central screw 130 is inserted through a bore 116 of the baseplate 110. Next, the coupling member 160 engages the baseplate 110 on a first end to secure the central screw 130 within the bore 116. The second end of the coupling member 160 is received within the glenosphere 180. Then, a post 200 may extend through the glenosphere 180 and the coupling member 160 and into the recess 136 of the central screw 130. The at least one peripheral screw 150 may be inserted through at least one peripheral bore 122 before securing the glenosphere 180 to the coupling member 160 with the post 200.

Figure 7:
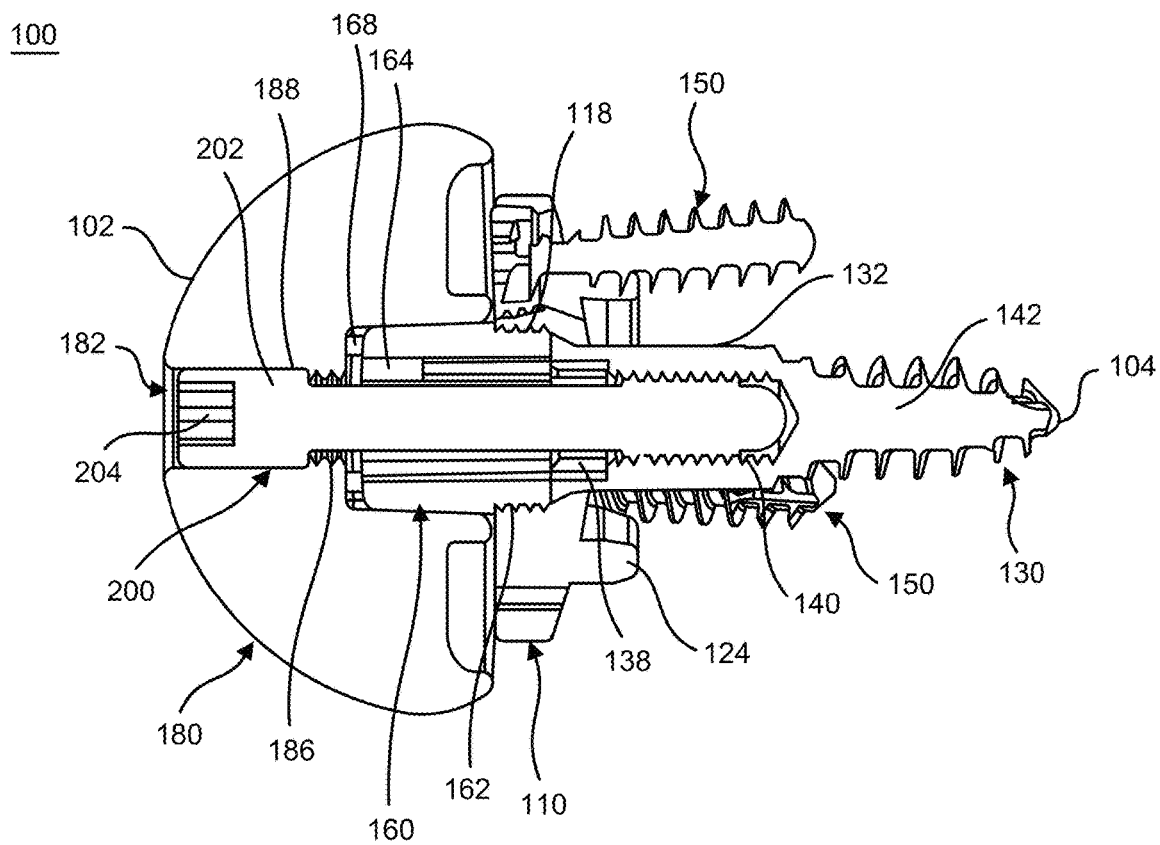
FIG. 7 is a first cross-sectional view of the glenoid implant of FIG. 1 taken along line 7-7 in FIG. 5, in accordance with an aspect of the present disclosure.
Figure 8:
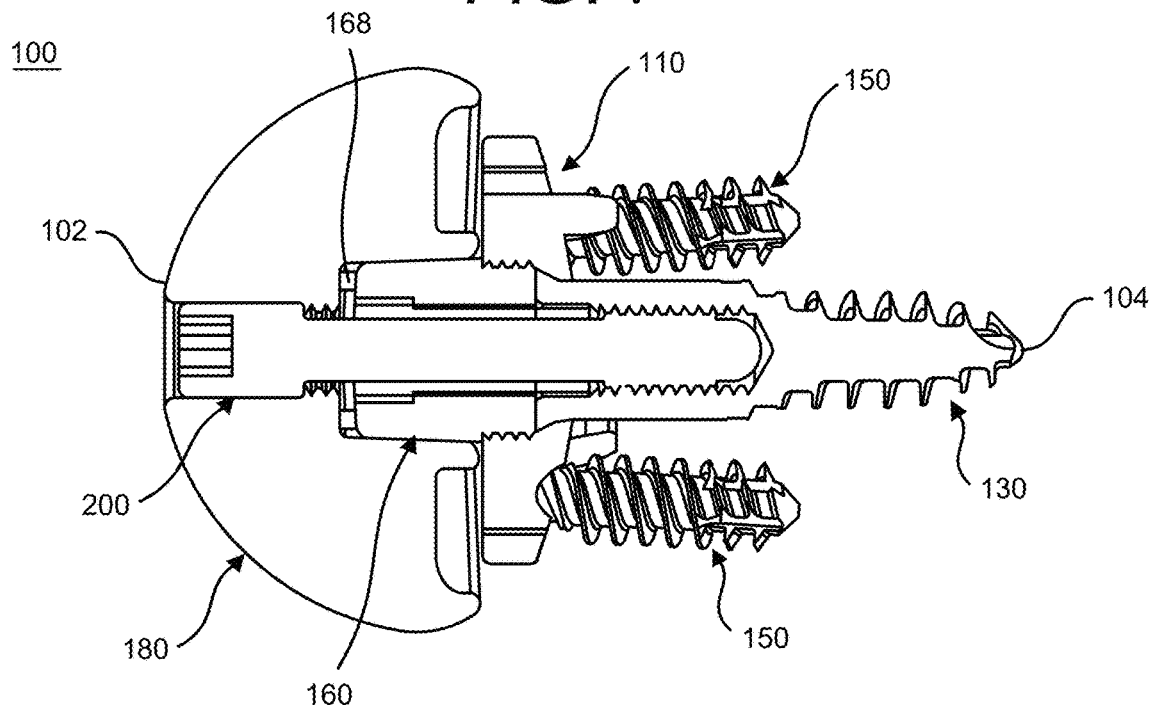
FIG. 8 is a second cross-sectional view of the glenoid implant of FIG. 1 taken along line 8-8 in FIG. 5, in accordance with an aspect of the present disclosure.
Figure 9:
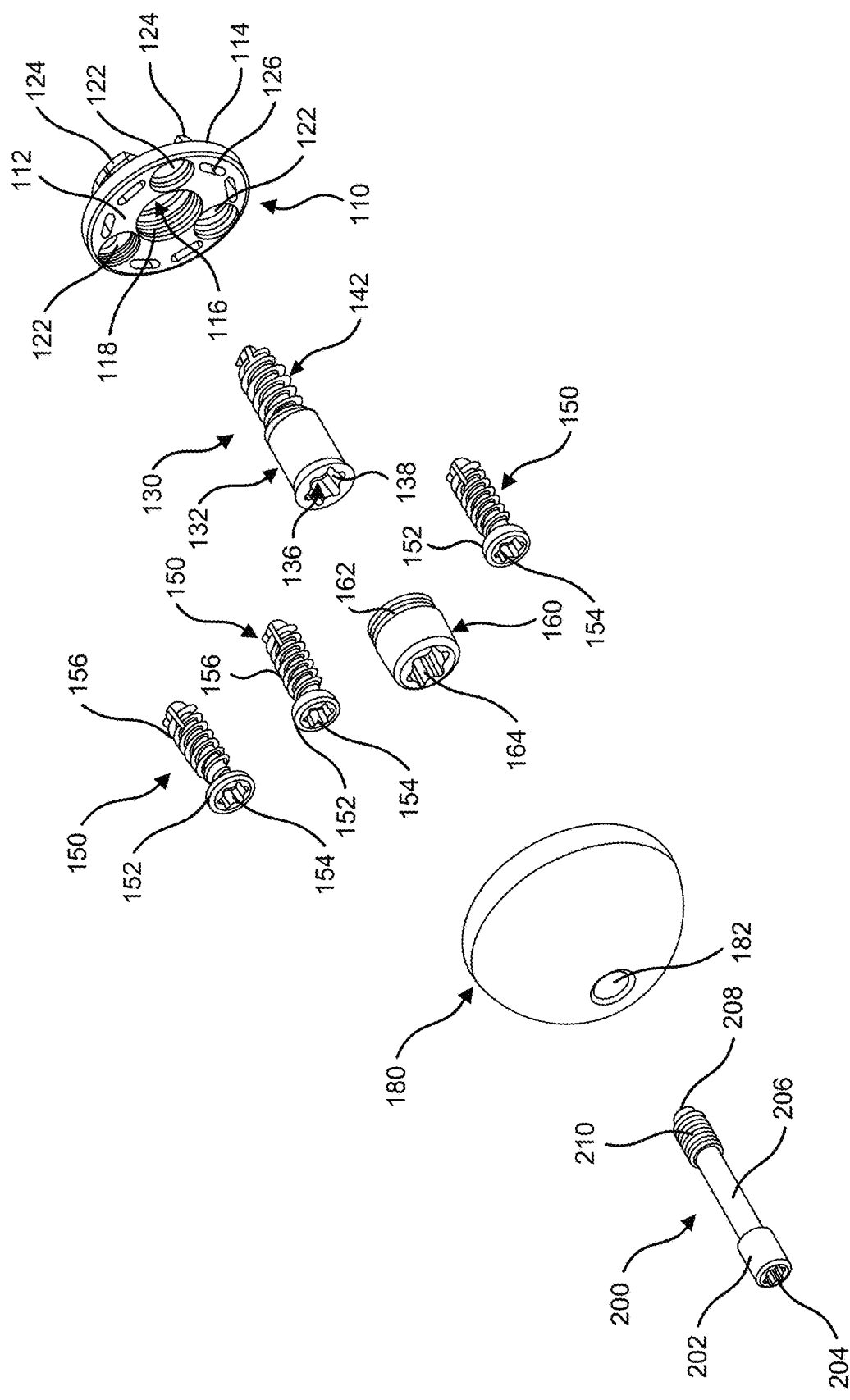
FIG. 9 is an exploded, first perspective view of the glenoid implant of FIG. 1, in accordance with an aspect of the present disclosure.
Figure 10:
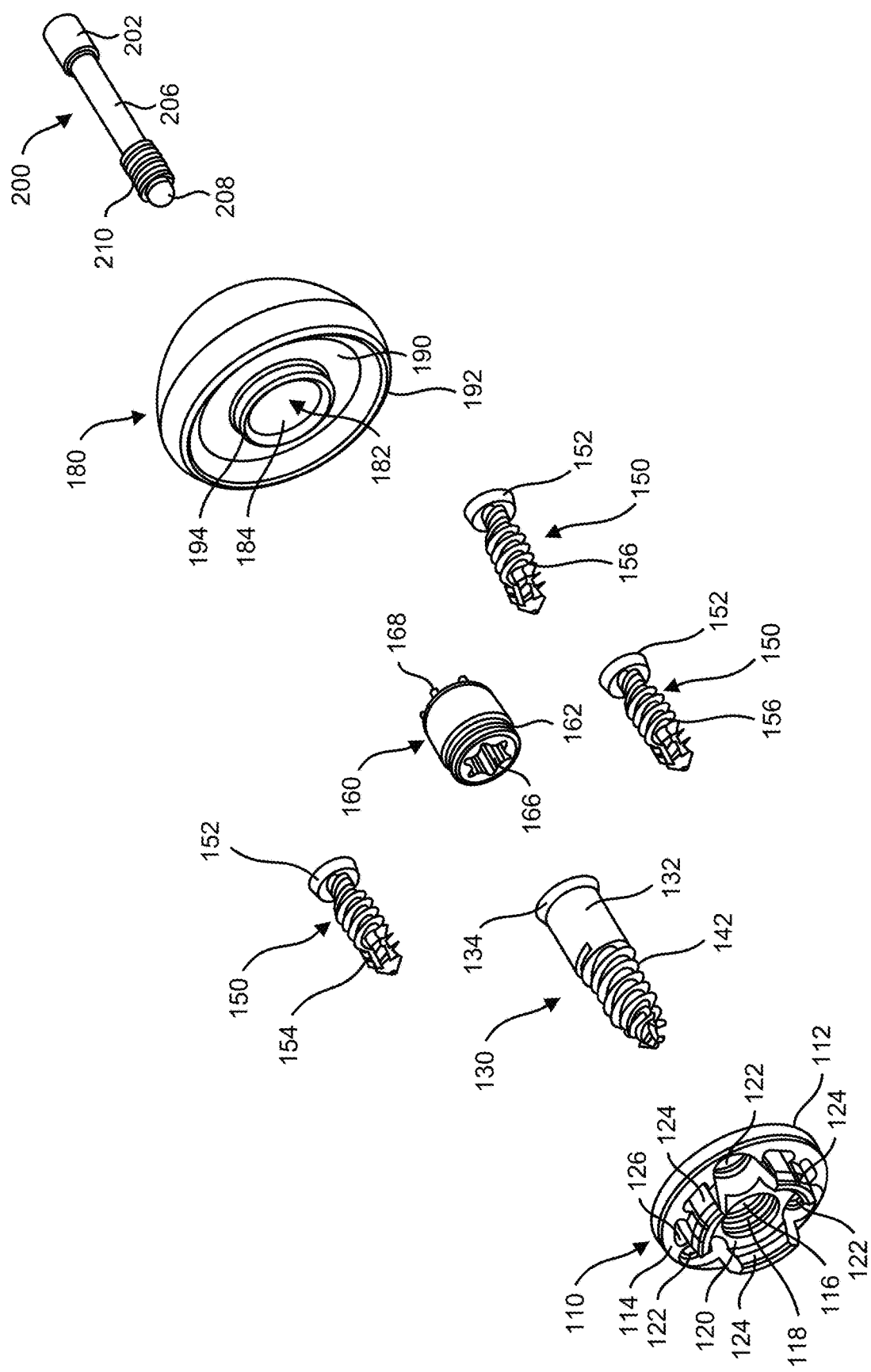
FIG. 10 is an exploded, second perspective view of the glenoid implant of FIG. 1, in accordance with an aspect of the present disclosure.
Figure 11:
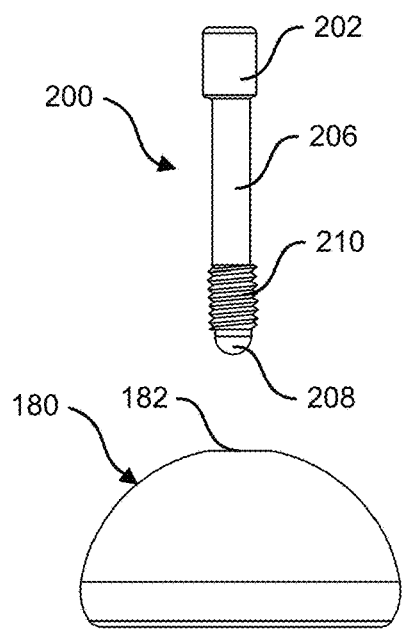
FIG. 11 is an exploded, first side view of the glenoid implant of FIG. 1, in accordance with the present disclosure.
Figure 11:
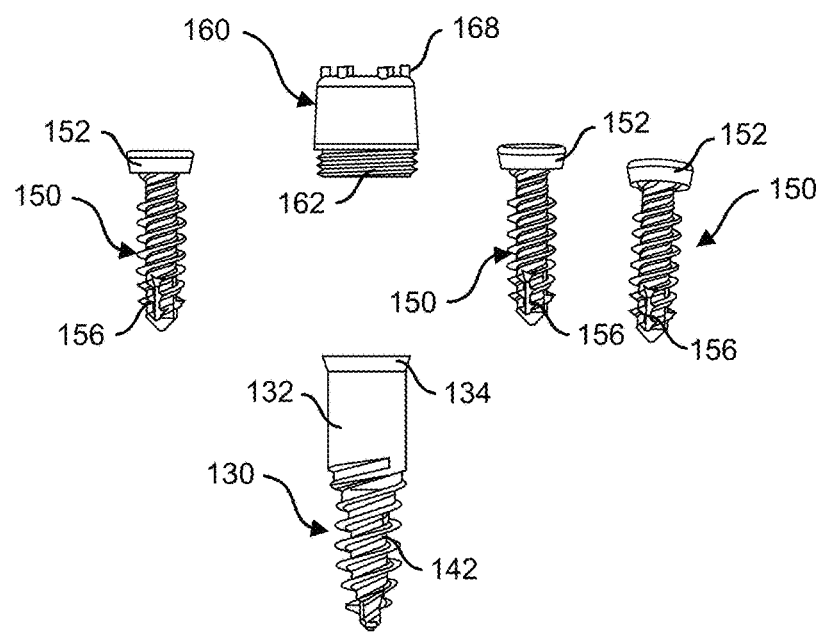
Figure 11:
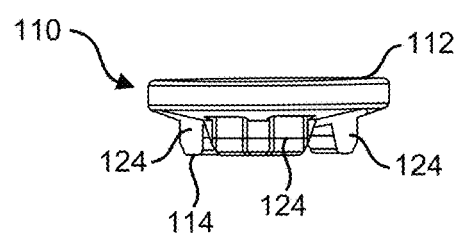
Figure 12:
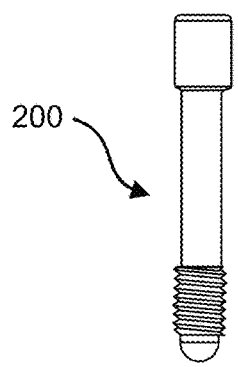
FIG. 12 is an exploded, second side view of the glenoid implant of FIG. 1, in accordance with an aspect of the present disclosure.
Figure 12:
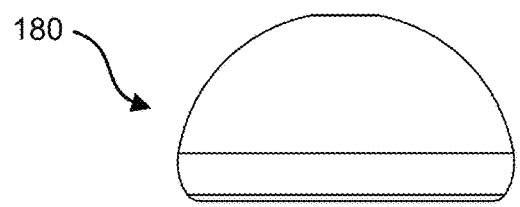
Figure 12:
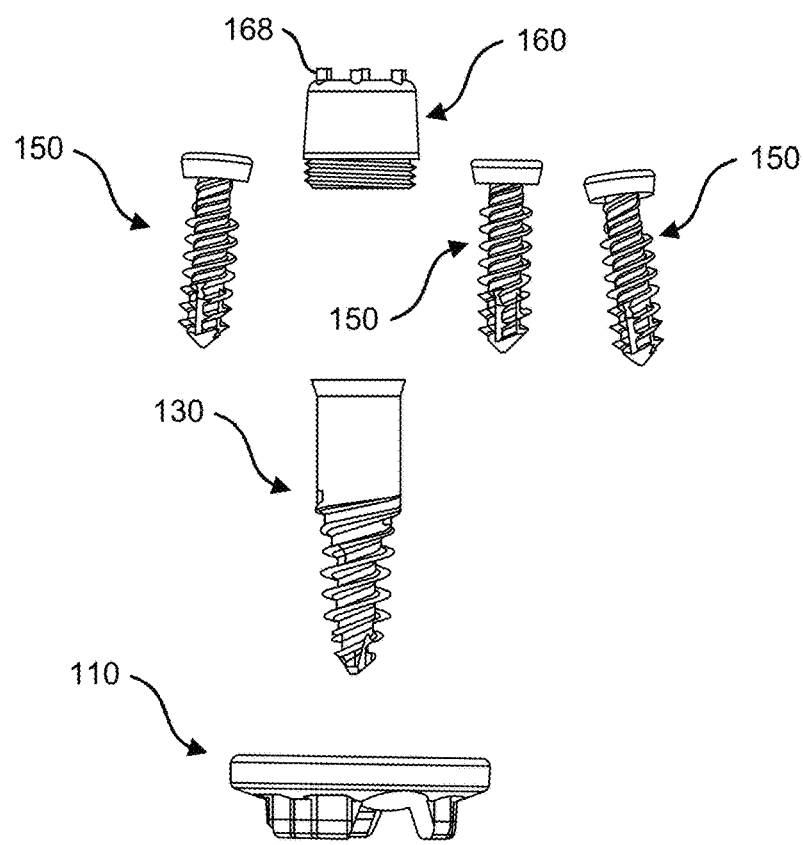
Figure 13:
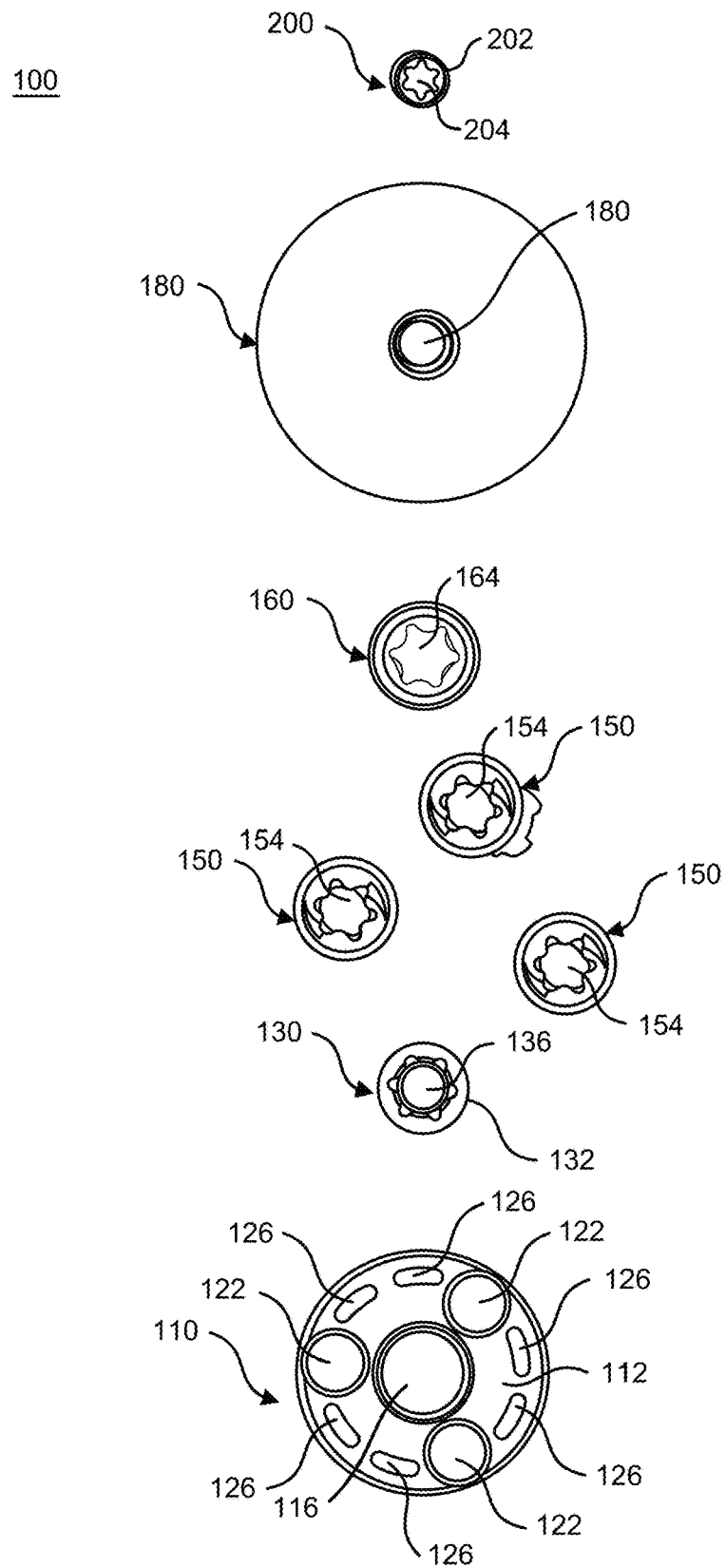
FIG. 13 is a lateral view of the glenoid implant of FIG. 1, in accordance with an aspect of the present disclosure.
Figure 14:
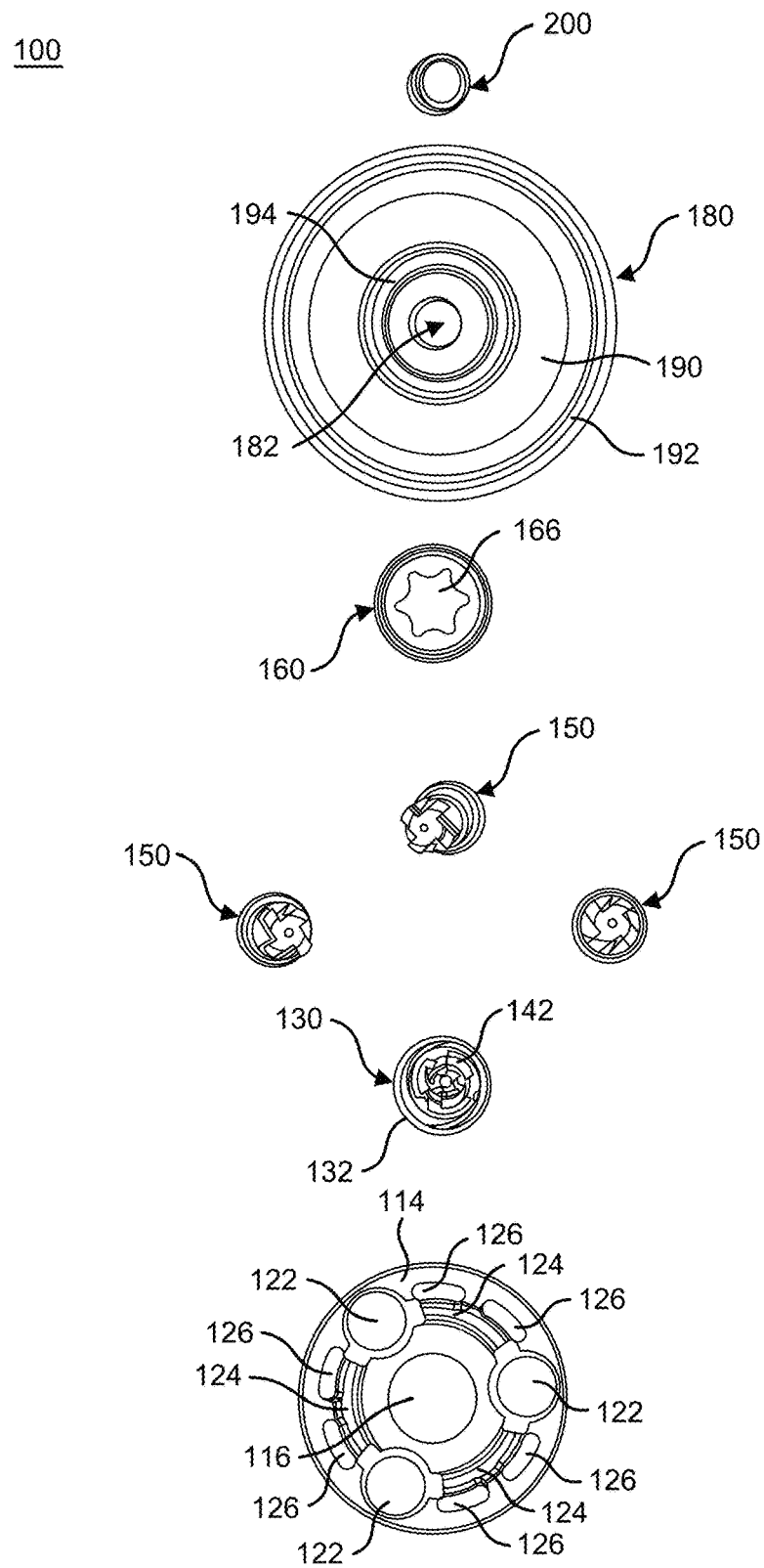
FIG. 14 is a medial view of the glenoid implant of FIG. 1, in accordance with an aspect of the present disclosure.
Figure 15:
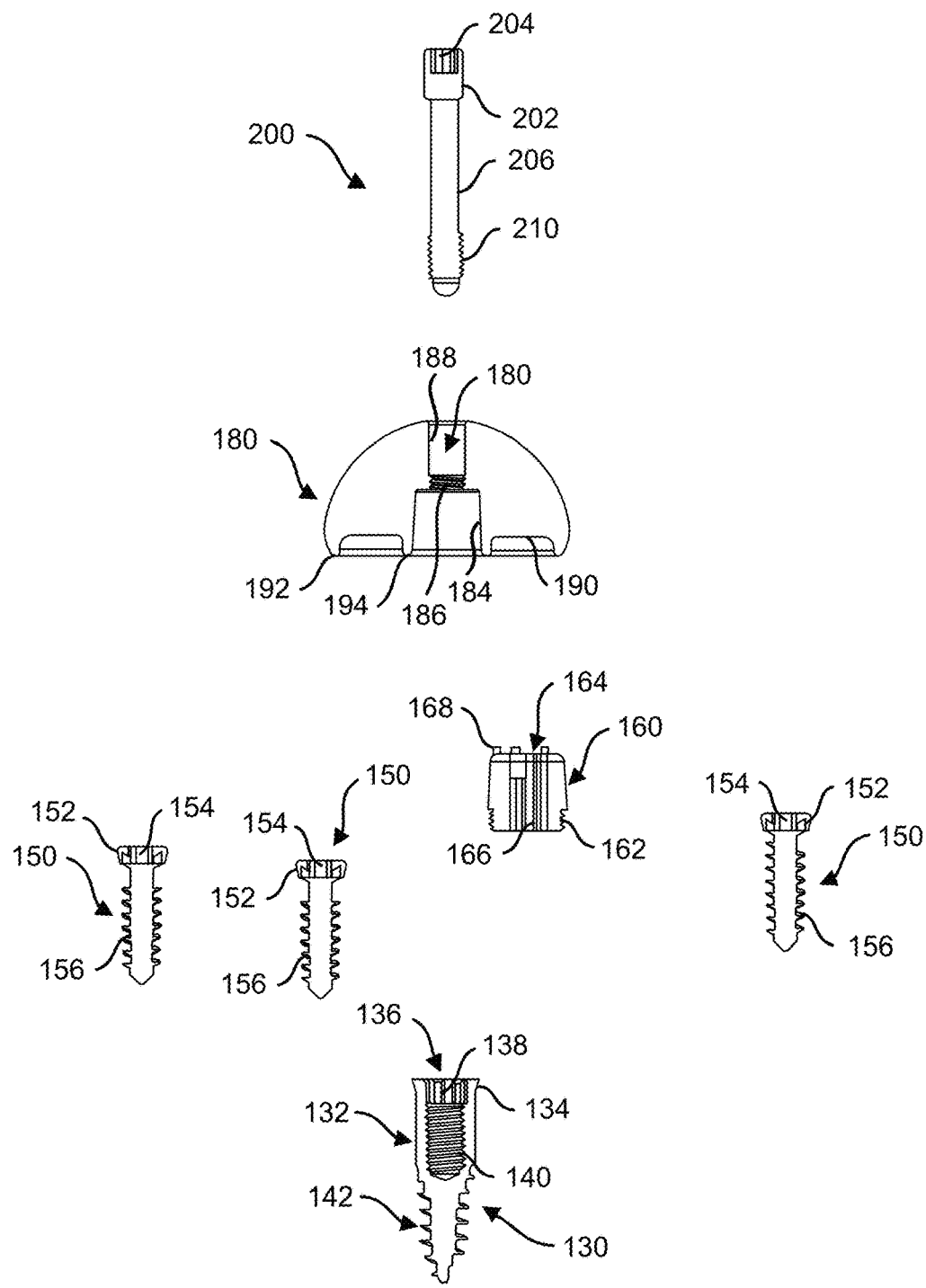
FIG. 15 is an exploded, cross-sectional side view of the components of the glenoid implant of FIG. 1, in accordance with an aspect of the present disclosure.
Figure 17:
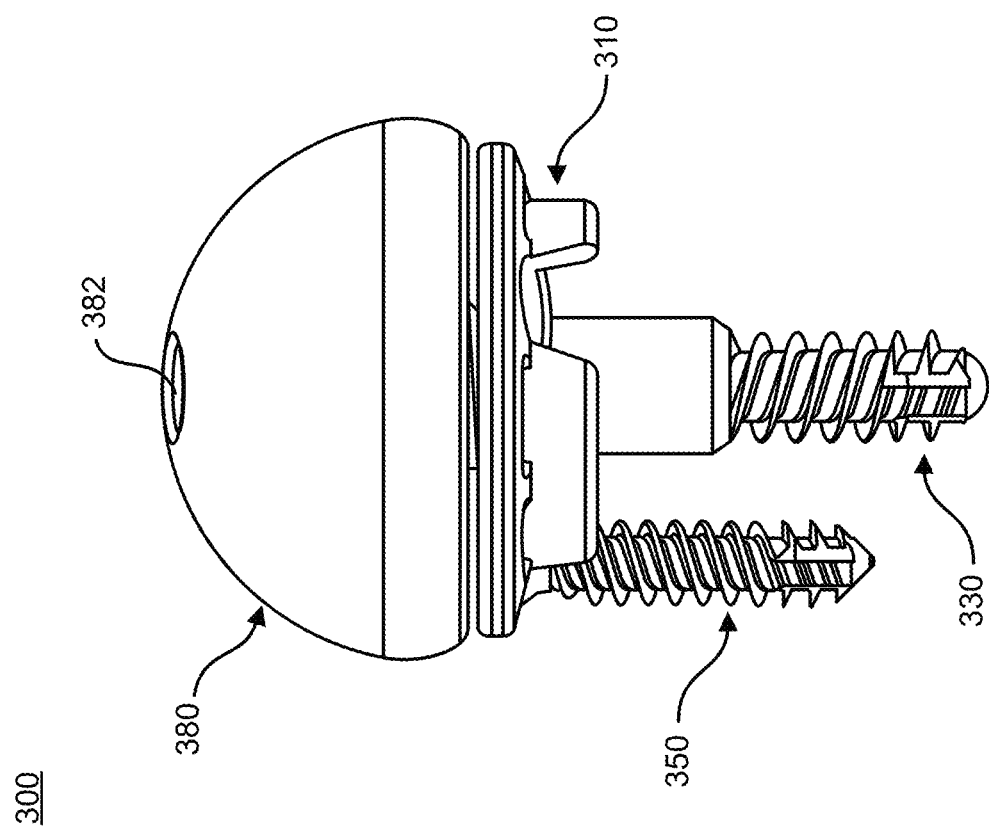
FIG. 17 is another side view of the glenoid implant of FIG. 16, in accordance with an aspect of the present disclosure.
Figure 16:
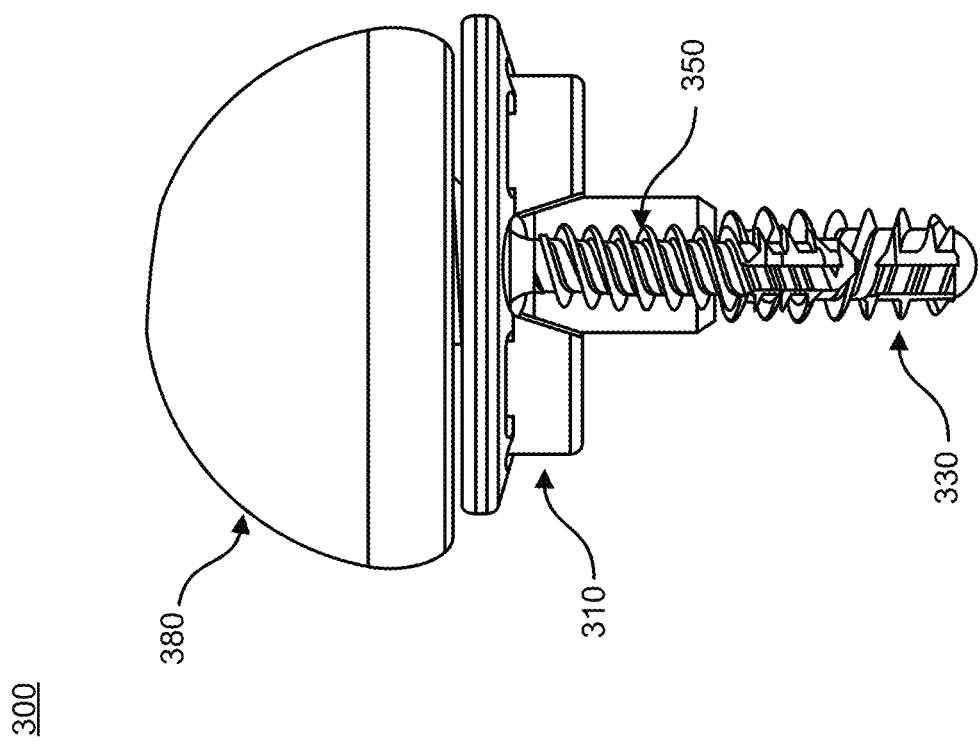
FIG. 16 is a side assembly view of another glenoid implant, in accordance with an aspect of the present disclosure.
Figure 19:
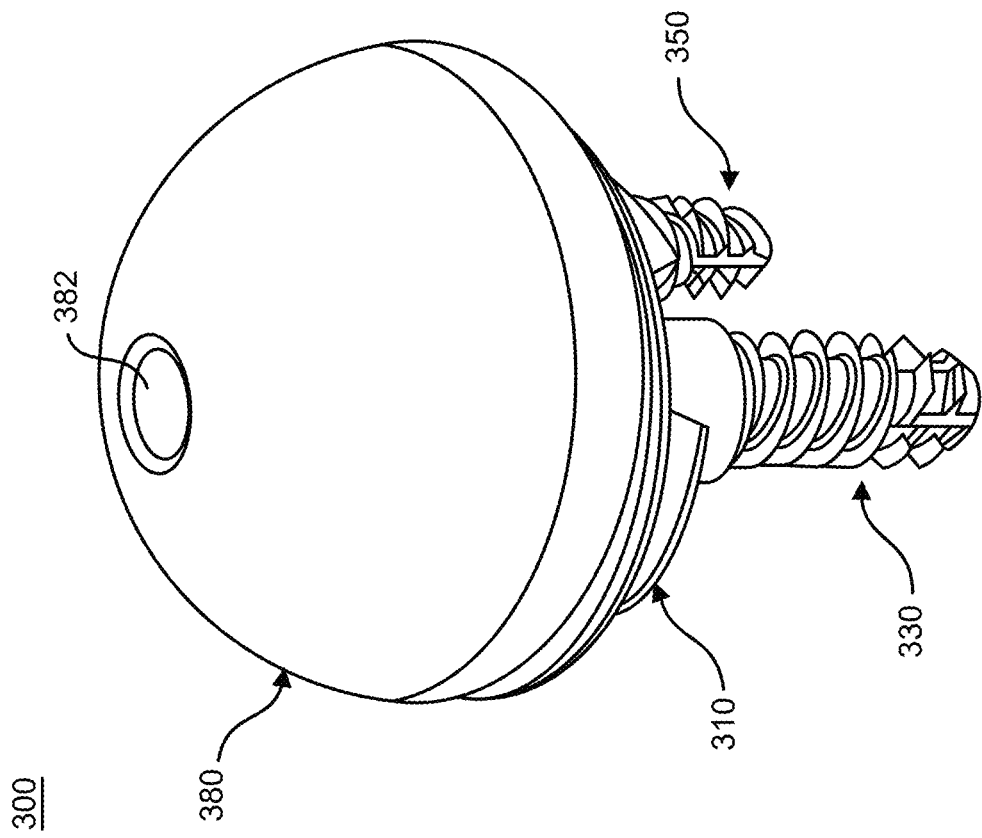
FIG. 19 is a top perspective view of the glenoid implant of FIG. 16, in accordance with an aspect of the present disclosure.
Figure 18:
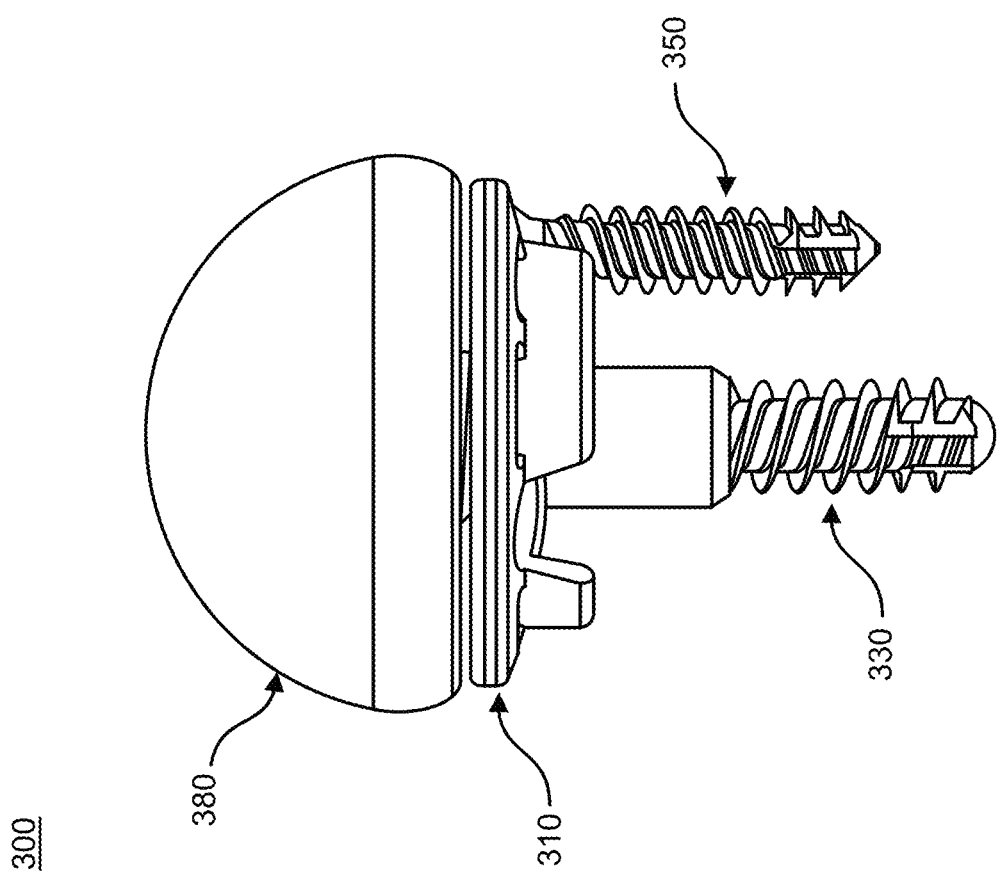
FIG. 18 is yet another side view of the glenoid implant of FIG. 16, in accordance with an aspect of the present disclosure.

With continued reference to FIGS. 7-15, the baseplate 110 includes an upper surface 112 with a cylindrical shape and a lower surface or bottom surface 114. The baseplate 110 may include, for example, a constant or continuous exterior ring surrounding the boards 122 and keels 124. The baseplate 110 may also include a central bore 116 extending through the baseplate 110 from the upper surface 112 to the lower surface 114. As shown in FIGS. 7, 8 and 15, the central bore 116 may include, for example, a first section or proximal interior threaded section 118 extending into the baseplate 110 from the upper surface 112. In addition, the central bore 116 may include, for example, a second section or distal non-threaded section 120 extending from the first section 118 to the lower surface 114 of the baseplate 110. The baseplate 110 may also include a plurality of peripheral bores 122 extending through the baseplate 110 from the upper surface 112 to the lower surface 114. The bores 122 may be positioned, for example, equally spaced around the circumference of the baseplate 110 or alternatively, not equally spaced around the circumference of the baseplate 110. In the depicted embodiment, the plurality of peripheral bores 122 includes three peripheral bores 122. The bottom surface 114 of the baseplate 110 may be, for example, curved or arced. The baseplate 110 may also include a plurality of discrete arcuate keels, ridges, or protrusions 124. The protrusions 124 may extend away from the bottom surface 114 of the baseplate 110. The baseplate 110 may also include a plurality of through openings 126 extending through the baseplate 110 from the upper surface 112 to the lower surface 114. The through openings 126 may, for example, be positioned between the plurality of peripheral boards 122 and positioned adjacent to the plurality of protrusions 124 on the lower surface 114 of the baseplate 110.

The central screw 130 as shown in FIGS. 7-15 may include a proximal non-threaded section 132 and a distal threaded section 142. The distal threaded section 142 may extend away from a bottom of the proximal non-threaded section 132. The proximal section 132 may include a head portion 134 positioned at a first end of the central screw 130. The head portion 134 may have, for example, a diameter larger than the diameter of the main portion of the proximal section 132 of the central screw 130. The proximal section 132 may also include a recess 136 extending into the proximal section 132 from the first end of the central screw 130. The recess 136 may include a first section or proximal female section 138 and a second section or threaded portion 140. The first section 138 may extend from the first end of the central screw 130 toward the second end and the second section 140 may extend from a bottom of the first section 138 to a bottom of the recess 136. The first section 138 may be, for example, a drive feature for engaging a tool for inserting or removing the central screw 130. The second section 140 may be, for example, threaded for receiving a corresponding threads 210 of the post 200. The proximal section 132 may have, for example, a texture or coating to provide for porous fixation. The proximal section 132 may be, for example, configured or sized and shaped to conserve bone. The distal threaded section 142 may be, for example, threaded to engage a patient's bone to secure the baseplate 110 to the patient's bone, such as, the glenoid.

With continued reference to FIGS. 7-15, the at least one peripheral screw 150 is shown. The at least one peripheral screw 150 may include a head portion 152 with a drive opening 154 recessed into the head portion 152 from a first end of the peripheral screw 150. The at least one peripheral screw 150 may also include a threaded portion 156 extending away from a bottom surface of the head portion 152 to a second end of the peripheral screw 150. The at least one peripheral screw 150 may be, for example, three peripheral screws 150 as shown in the depicted embodiment. Although alternative numbers of peripheral screws 150 are also contemplated to correspond to the number of peripheral bores 122 in the baseplate 110. The peripheral screws 150 may be inserted through the peripheral bores 122 in the baseplate 110 to engage a patient's bone, such as, the glenoid, to assist with securing the baseplate 110 to the patient's bone.

The coupling member or modular taper 160 is shown in FIGS. 7-15. The coupling member 160 may include an exterior threaded portion 162 on the distal or second end of the coupling member 160. The coupling member 160 may also include a proximal recess 164 extending into the coupling member 160 from the first end. The coupling member 160 may also include a central bore 166 extending through the coupling member 160 from the first end to the second end. The proximal recess 164 may, for example, overlap with the central bore 166 at the first end of the coupling member 160.

With continued reference to FIGS. 7-15, the glenosphere 180 may include a central bore 182 extending through the glenosphere 180 from a first end to a second end. The central bore 182 may include a distal tapered portion 184, a central threaded portion 186, and a proximal cylindrical portion 188. The distal tapered portion 184 may extend from the second end of the glenosphere 180 toward the first end. The central threaded portion 186 may be positioned between the distal tapered portion 184 and the proximal cylindrical portion 188. The proximal cylindrical portion 188 may extend from the central threaded portion 186 two the first end of the glenosphere 180. As shown in FIGS. 7, 8 and 15, the diameter of the distal tapered portion 184 may be, for example, larger than the diameter of the proximal cylindrical portion 188. In addition, the diameter of the central threaded portion 186 may be smaller than the diameter of both the proximal cylindrical portion 188 and the distal tapered portion 184. The distal tapered portion 184 may include sidewalls that taper as they extend from the second end of the glenosphere 180 to the central threaded portion 186. The second end of the glenosphere 180 may include a recessed region 190 positioned between a first lip or exterior lip 192 and a protrusion 194. The first lip 192 may surround the circumference of the second end of the glenosphere 180. The first lip 192 may be, for example, a constant or continuous ring surrounding the recessed region 190. The protrusion 194 may surround the central bore 182 on the second end of the glenosphere 180.

The post 200 is shown in FIGS. 7-15. The post 200 may include a cylindrical proximal head 202 positioned at a first end of the post 200. The cylindrical proximal head 202 may include, for example, a proximal recess 204 extending into the proximal head 202 from the first and of the post 200. The post 200 may also include a central portion 206 extending away from a second end of the proximal head 202. Further, the post 200 may include a distal portion 208 positioned at a second end of the post 200. The post 200 may also include an exterior threaded portion 210 positioned between the central portion 206 and a distal portion 208. The threaded portion 210 may be, for example, configured or sized and shaped to engage the second threaded section 140 of the central screw 130.

As shown in FIGS. 1-6, the implant 100 may be assembled by, for example, inserting the central screw 130 through the central bore 116 of the baseplate 110. The threaded portion 162 of the coupling member 160 may then be threaded into the proximal interior threaded section 118 of the baseplate 110 to secure the central screw 130 to the baseplate 110. After the baseplate 110, central screw 130, and the coupling member 160 are secured together they may be, for example, inserted into a patient coupled together. The at least one peripheral screw 150 may then be inserted through the plurality of peripheral bores 122 of the baseplate 110. Next, the distal tapered portion 184 of the glenosphere 180 may be coupled to the proximal end of the coupling member 160. The coupling member 160 may, for example, allow for angulation of the peripheral screws 150 before the coupling member 160 is attached to assist in preventing the central screw 130 from coming out when the glenosphere 180 is attached. A post 200 may then be inserted through the central bore 182 of the glenosphere 180, the central bore 166 of the coupling member 160 and into the recess 136 of the central screw 130 such that the threaded portion 210 of the post 200 engages the threaded portion 140 of the central screw 130.

A surgical method for implanting the glenoid implants 100, 300, may include preparing the patient's joint by performing sizing and alignment steps. Next, the bone may be reamed to form a channel and recess to receive the glenoid implant 100, 300. Next the selected glenoid implant 100, 300 may be inserted and coupled to the bones. Finally, the surgical procedure may be completed and the patient's incision may be closed.

Figure 21:
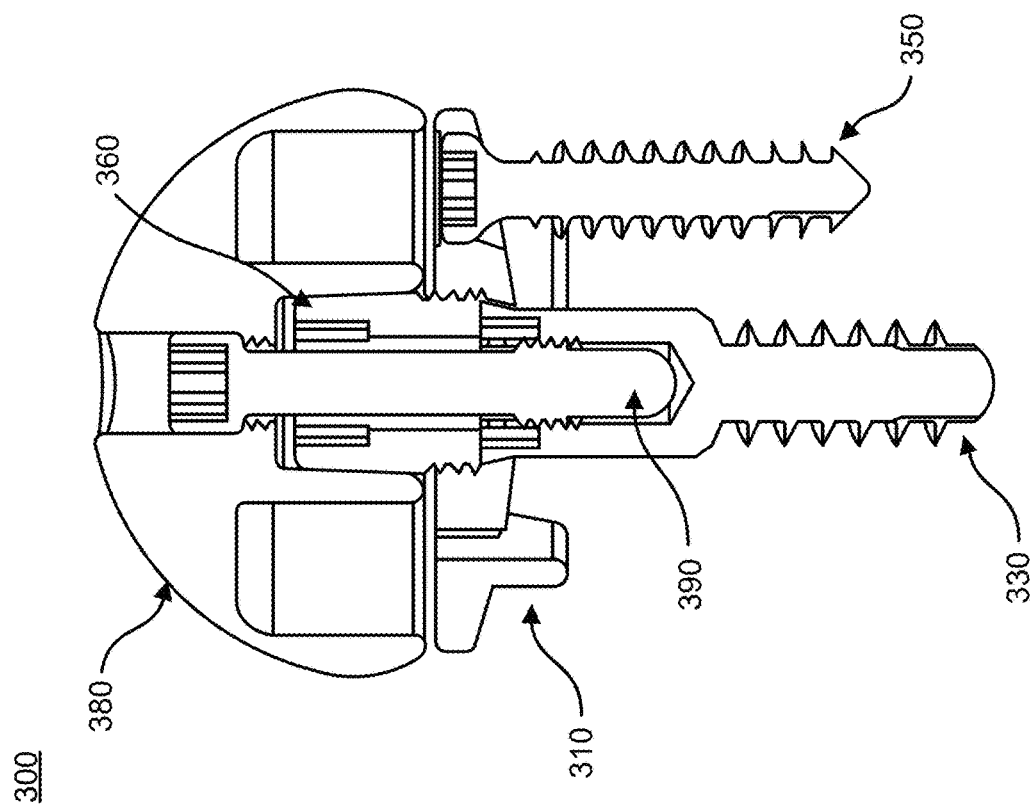
FIG. 21 is a side cross-sectional view of the glenoid implant of FIG. 16, in accordance with an aspect of the present disclosure.
Figure 20:
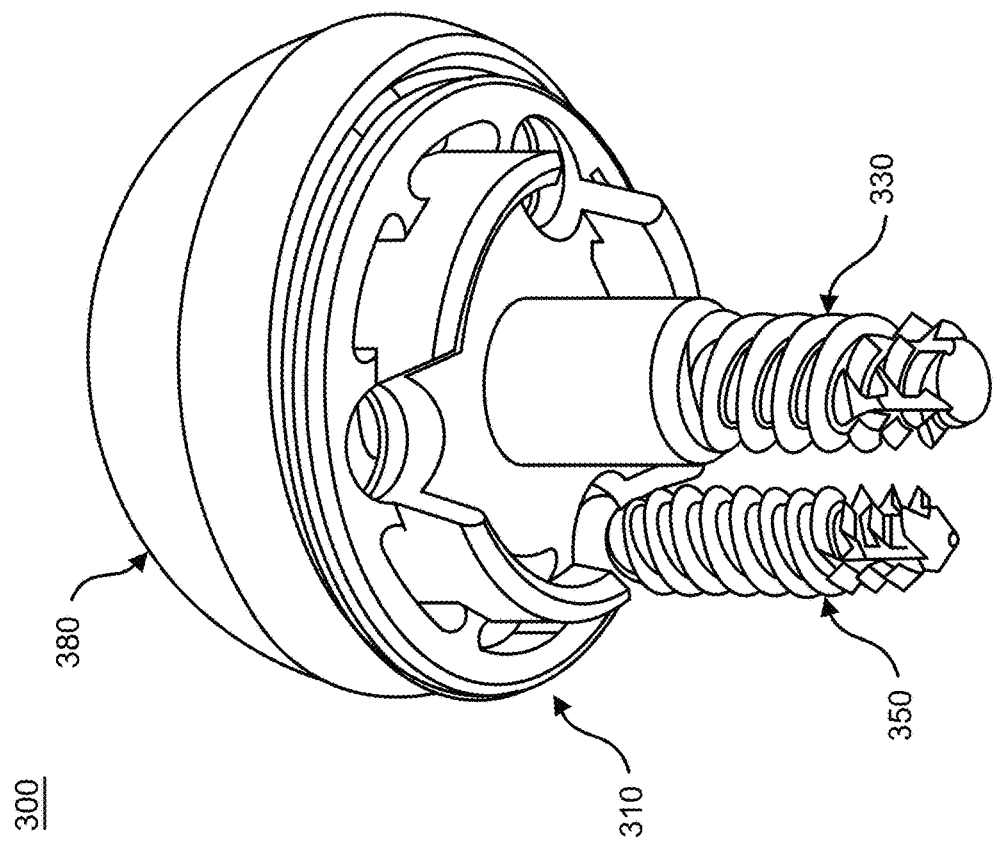
FIG. 20 is a bottom perspective view of the glenoid implant of FIG. 16, in accordance with an aspect of the present disclosure.
Figure 22:
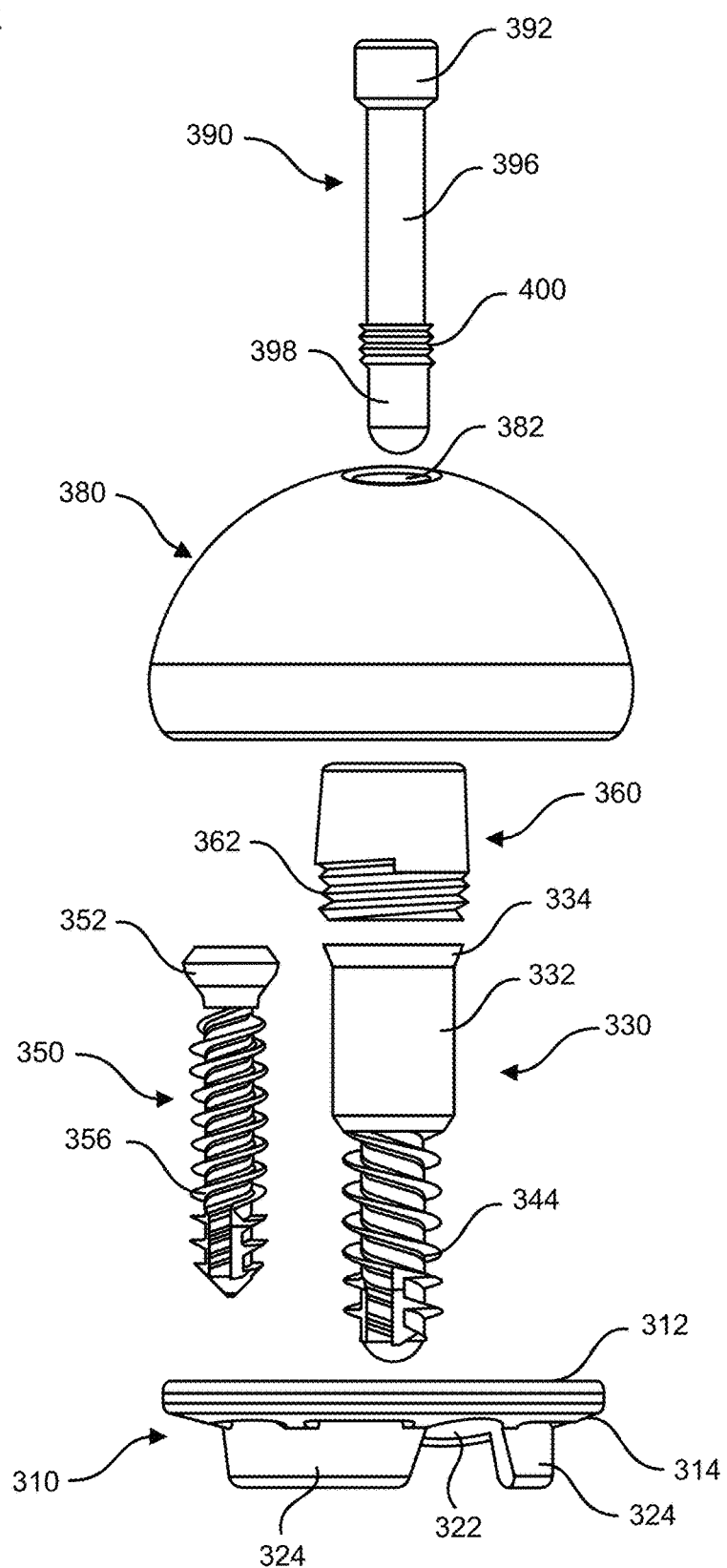
FIG. 22 is an exploded, side view of the glenoid implant of FIG. 16, in accordance with an aspect of the present disclosure.
Figure 23:
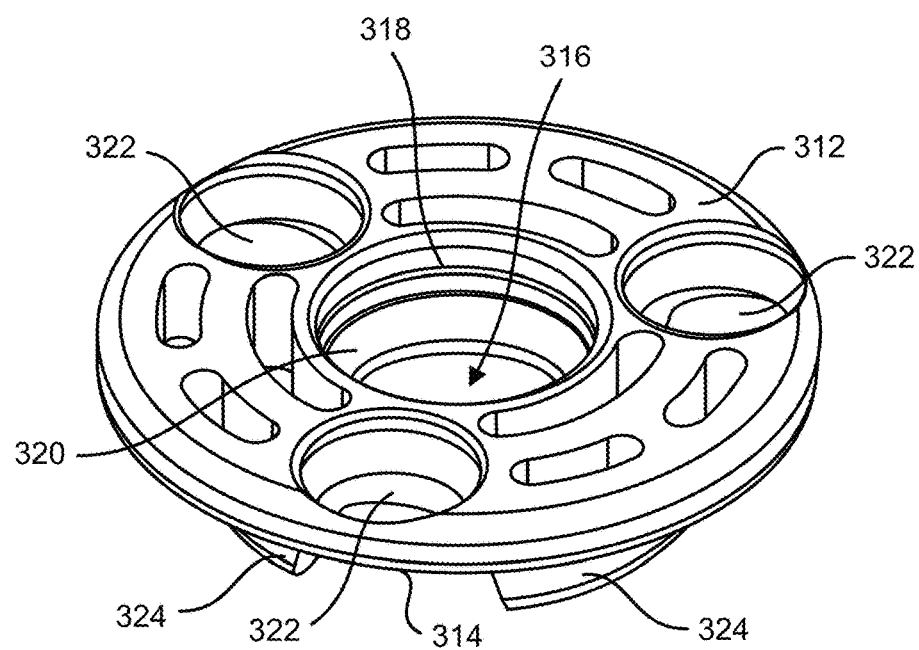
FIG. 23 is a top perspective view of a baseplate of the glenoid implant of FIG. 16, in accordance with an aspect of the present disclosure.
Figure 24:
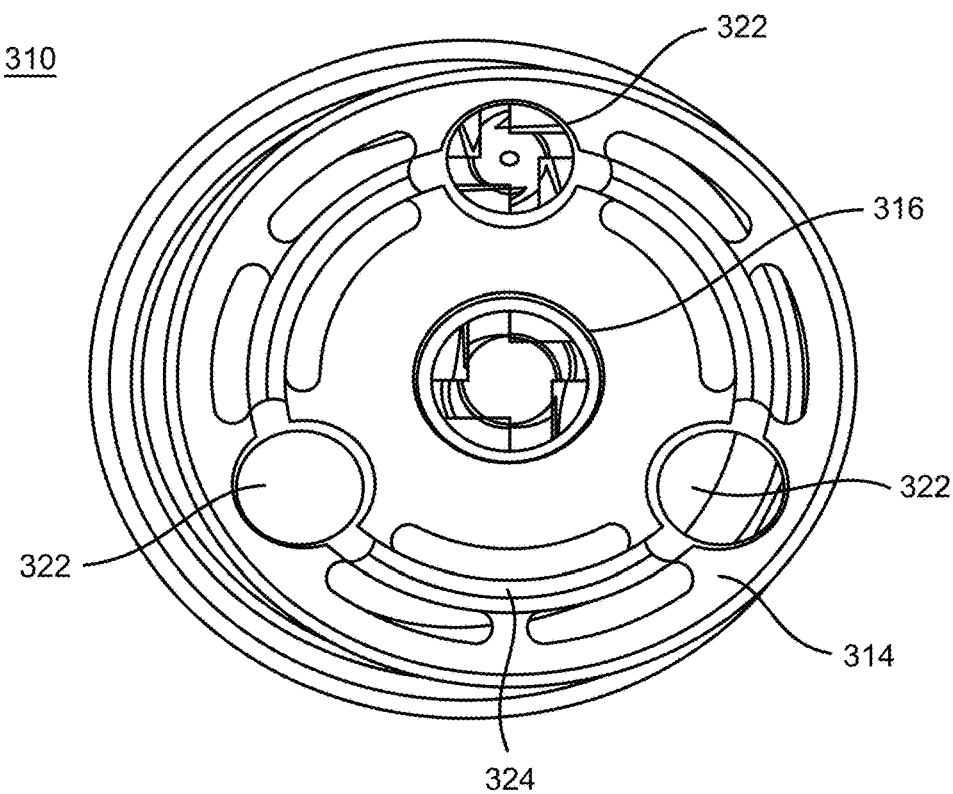
FIG. 24 is a bottom view of the baseplate of FIG. 23, in accordance with an aspect of the present disclosure.
Figure 25:
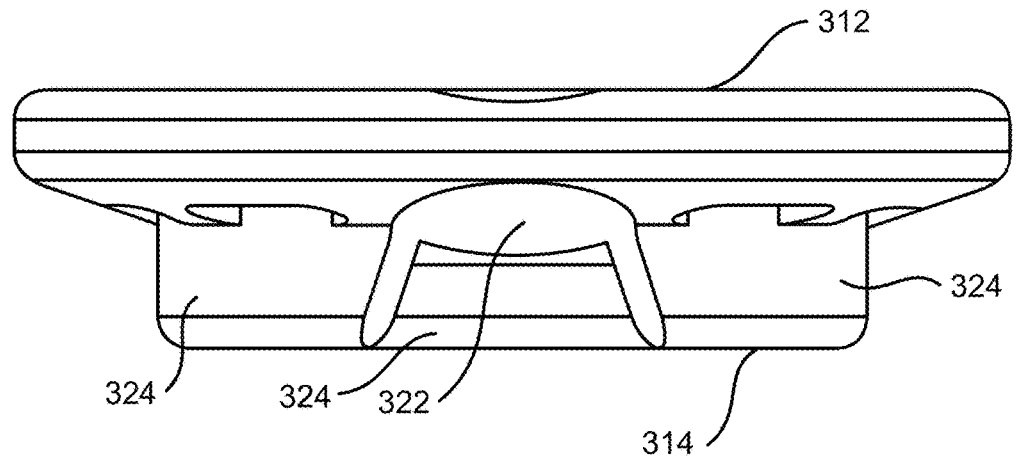
FIG. 25 is a side view of the baseplate of FIG. 23, in accordance with an aspect of the present disclosure.
Figure 26:
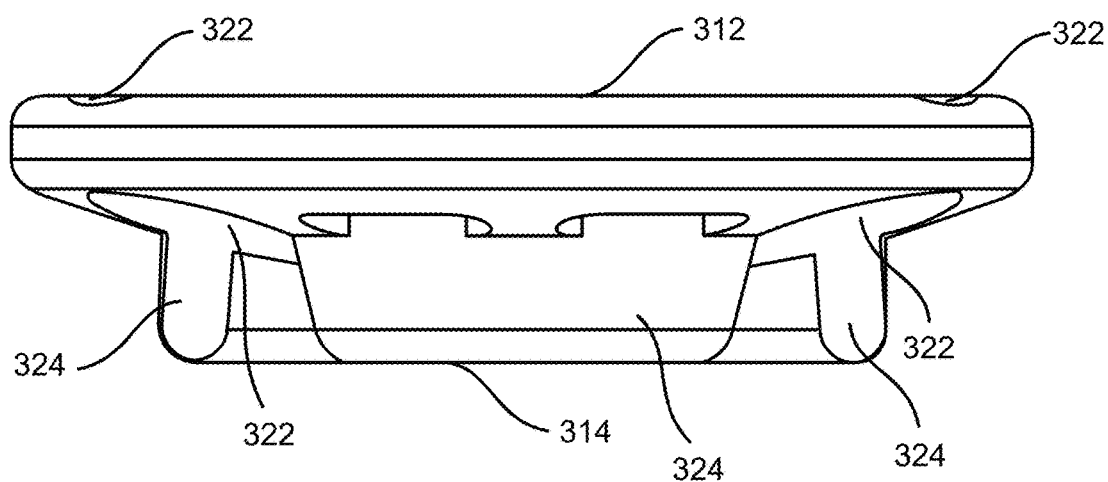
FIG. 26 is another side view of the baseplate of FIG. 23, in accordance with an aspect of the present disclosure.
Figure 27:
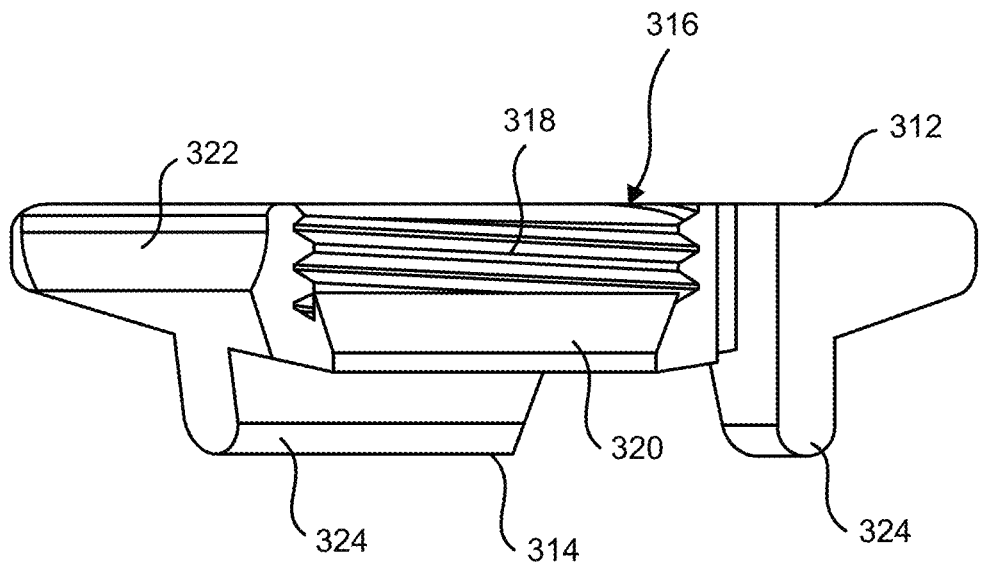
FIG. 27 is another side view of the baseplate of FIG. 23, in accordance with an aspect of the present disclosure.

Referring now to FIGS. 16-45, another embodiment of a glenoid implant or reverse glenoid implant 300. As shown in FIGS. 21-22, the glenoid implant 300 includes a baseplate 310, a central screw 330, a peripheral compression screw 350, a modular taper 360, a glenosphere 380, and a post 390.

Figure 28:
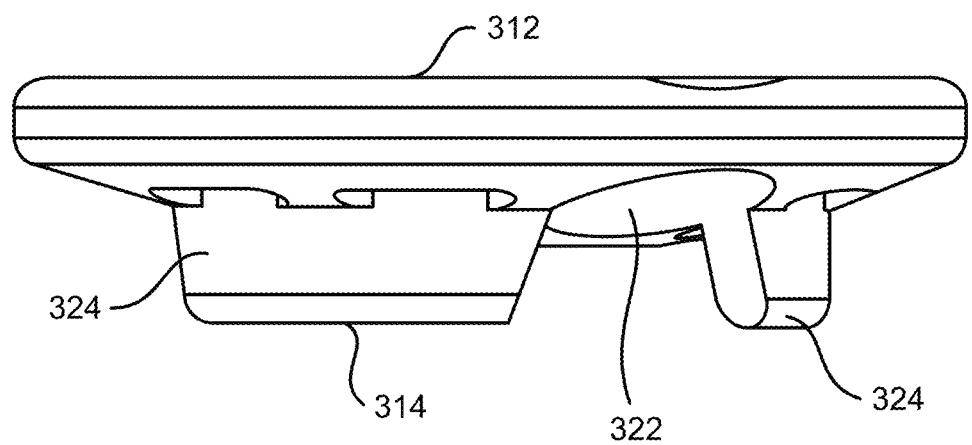
FIG. 28 is a cross-sectional side view of the baseplate of FIG. 23, in accordance with an aspect of the present disclosure.

Referring now to FIGS. 23-28, the baseplate 310 includes a cylindrical shape, an upper surface 312 and a lower or bottom surface 314. The baseplate 310 also includes a central bore 316 extending between the upper surface 312 and the lower surface 314. The baseplate 310 also includes a plurality of peripheral bores 322 disposed around the central bore 316. In addition, the baseplate includes a plurality of discrete arcuated keels 324 extending away from the bottom surface 314 of the baseplate 310. As illustrated in FIG. 28, the central bore 316 of the baseplate 310 includes a proximal interior threaded section 318 and a distal non-threaded section 320.

Figure 31:
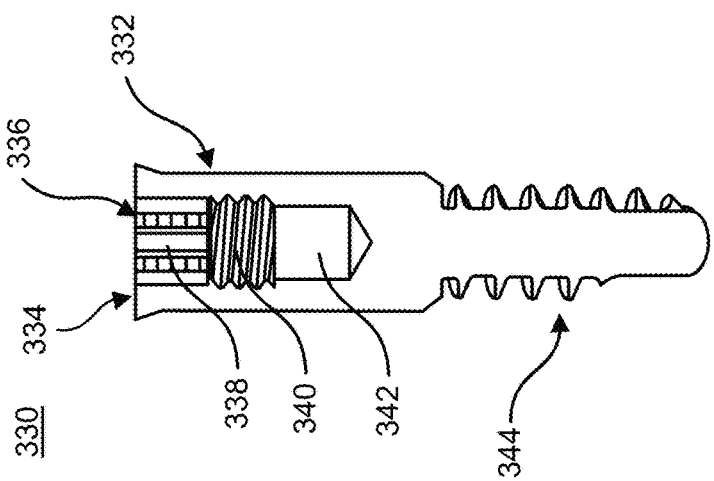
FIG. 31 is a cross-sectional side view of the central screw of FIG. 29, in accordance with an aspect of the present invention.
Figure 30:
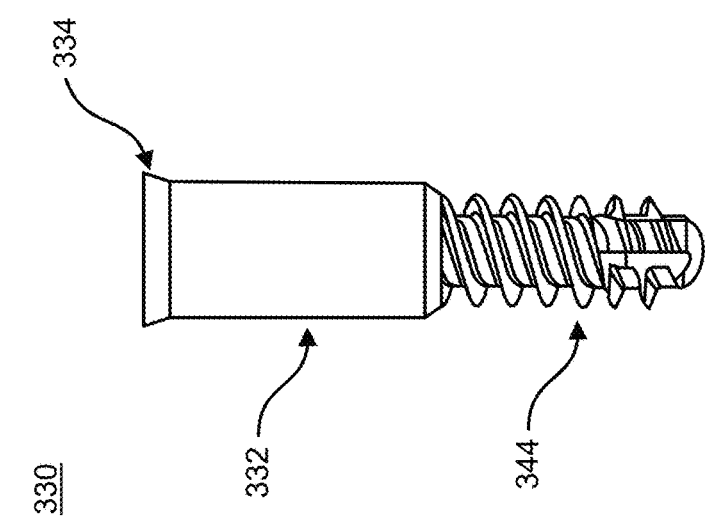
FIG. 30 is a side view of the central screw of FIG. 29, in accordance with an aspect of the present disclosure.
Figure 29:
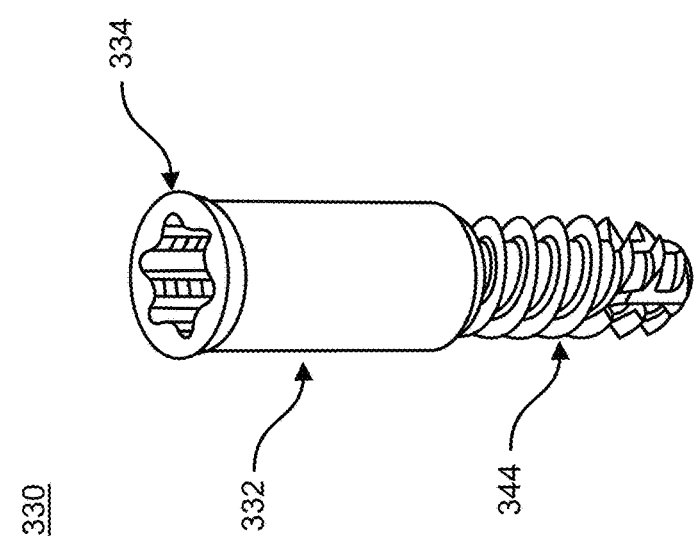
FIG. 29 is a top perspective view of a central screw for use with the glenoid implant of FIG. 16, in accordance with an aspect of the present disclosure.

Referring now to FIGS. 29-31, the central screw 330. The central screw 330 includes a central axis, a proximal non-threaded section 332 having a cylindrical shape, and a distal threaded section 344. The central screw 330 may include any desired length or width as can the proximal non-threaded section 332 and/or the distal threaded section 344. Advantageously, a reverse glenoid system may include a plurality of central screws 330 having varying overall lengths and varying section lengths. The non-threaded section 342 of the central screw 330 may further include a bone ingrowth surface including texturing, pores, holes, and/or a sprayed on mechanical or biological bone ingrowth promoting material. The central screw 330 also includes a proximal head portion 334. The head portion 334 has a surface area that increases in a direction opposite threaded portion 342. The head portion 334 of the central screw 330 includes a recess 336 that includes a proximal female section 338 for engaging a torque device (such as a screw driver). The recess 336 includes a central threaded portion 340, and a distal non-threaded portion 342. The recess 336 is disposed through proximal head 334. As illustrated in FIGS. 21 and 22, the central screw 330 is slidingly disposed through the central bore 316 of the baseplate 310. The diameter of the head 334 is greater than a diameter of non-threaded section 332 of the central bore 316 of the baseplate 310 such that the central screw 330 is captured by the baseplate central bore 316. The central screw 330 is, for example, suitable for threading into a bone.

Figure 34:
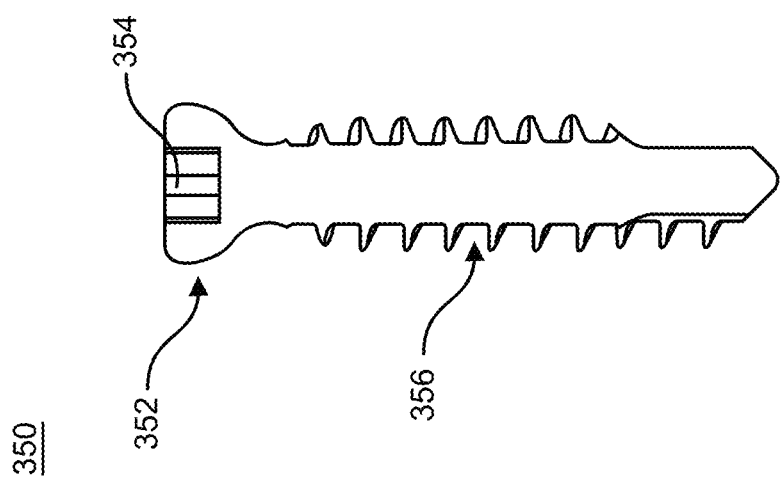
FIG. 34 is a cross-sectional side view of the peripheral compression screw of FIG. 32, in accordance with an aspect of the present disclosure.
Figure 33:
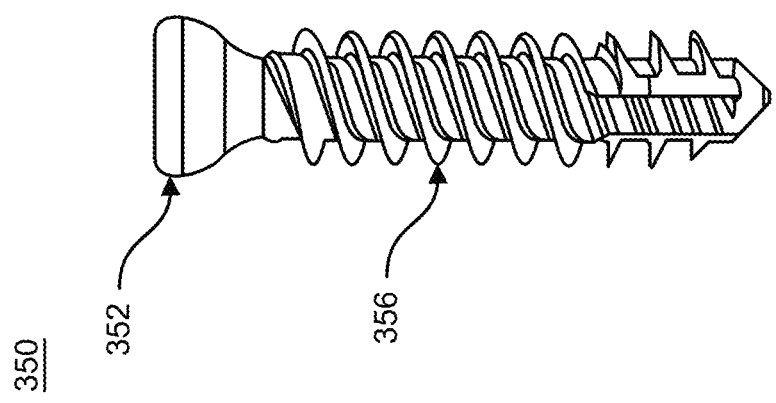
FIG. 33 is a side view of the peripheral compression screw of FIG. 32, in accordance with an aspect of the present disclosure.
Figure 32:
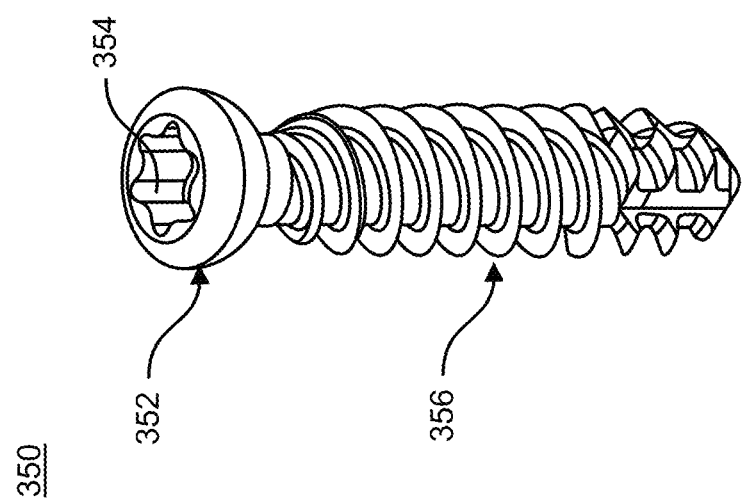
FIG. 32 is a top perspective view of a peripheral compression screw for use with the glenoid implant of FIG. 16, in accordance with an aspect of the present disclosure.

Referring now to FIGS. 32-34, a peripheral screw 350 is shown. The screw 350 may be, for example, a standard compression screw of the type known in the orthopedic implant arts. The peripheral screw 350 may include a head portion 352, a drive opening 354 inset into the head portion 352 at a first end of the screw 350, and a threaded portion 356 extending away from the head portion 352. Each screw 350 is insertable through at least one of the peripheral bores 322 of the baseplate 310 and into a desired bone to compress the implant 300 onto the bone.

Figure 35:
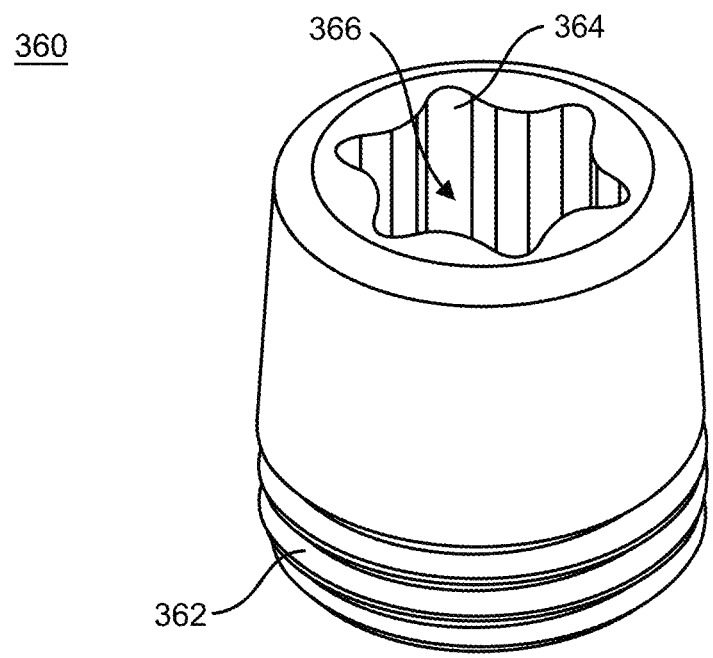
FIG. 35 is a top perspective view of a modular locking taper for use with the glenoid implant of FIG. 16 of FIG. 32, in accordance with an aspect of the present disclosure.
Figure 36:
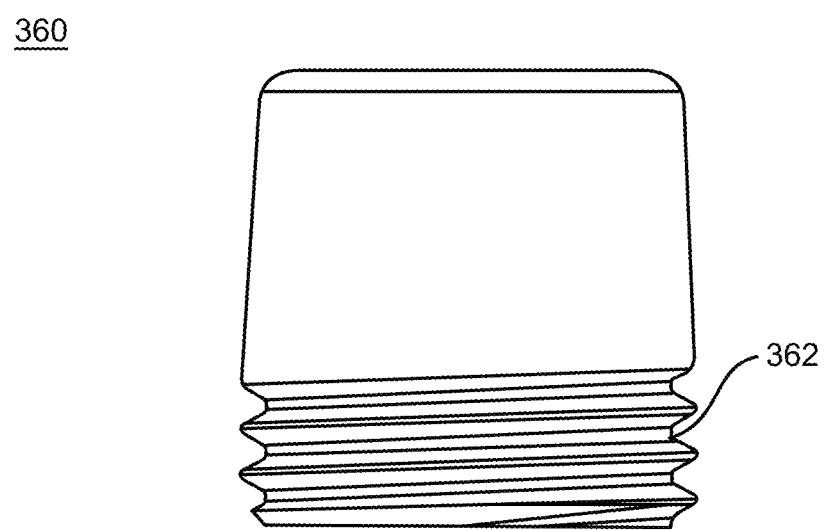
FIG. 36 is a side view of the modular locking taper of FIG. 35, in accordance with an aspect of the present disclosure.
Figure 37:
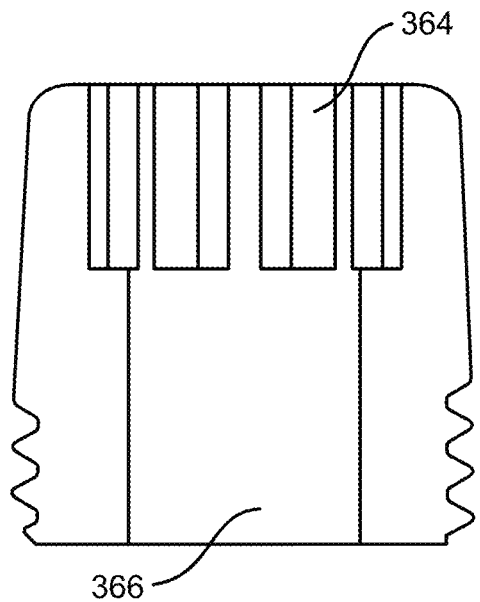
FIG. 37 is a cross-sectional side view of the modular locking taper of FIG. 35, in accordance with an aspect of the present disclosure.
Figure 38:
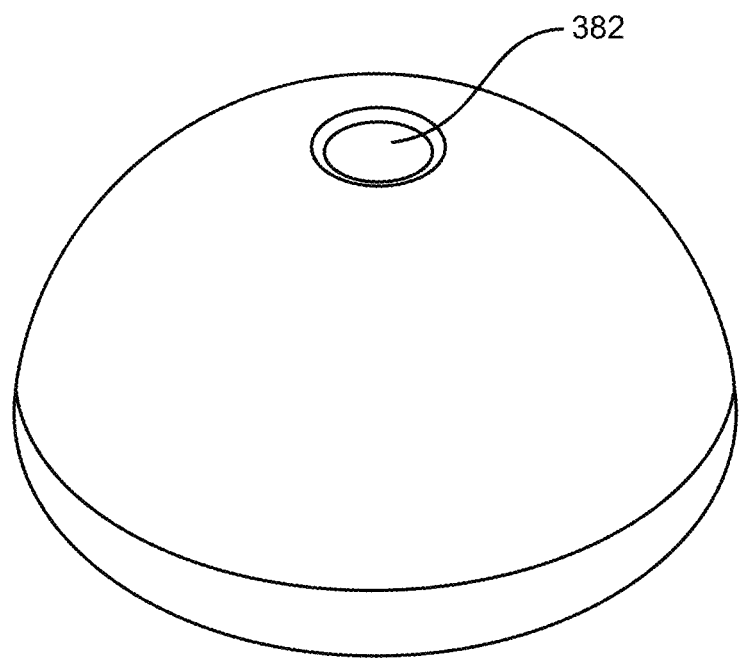
FIG. 38 is a top perspective view of a glenosphere of the glenoid implant of FIG. 16, in accordance with an aspect of the present disclosure.
Figure 39:
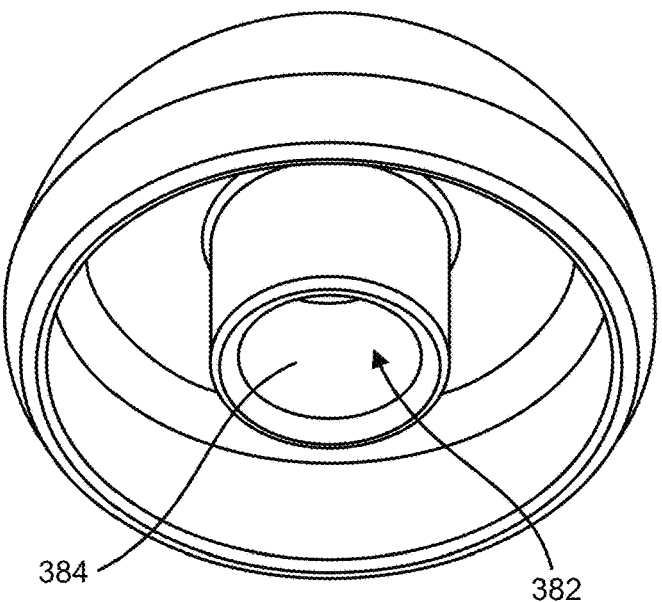
FIG. 39 is a bottom perspective view of the glenosphere of FIG. 38, in accordance with an aspect of the present disclosure.
Figure 40:
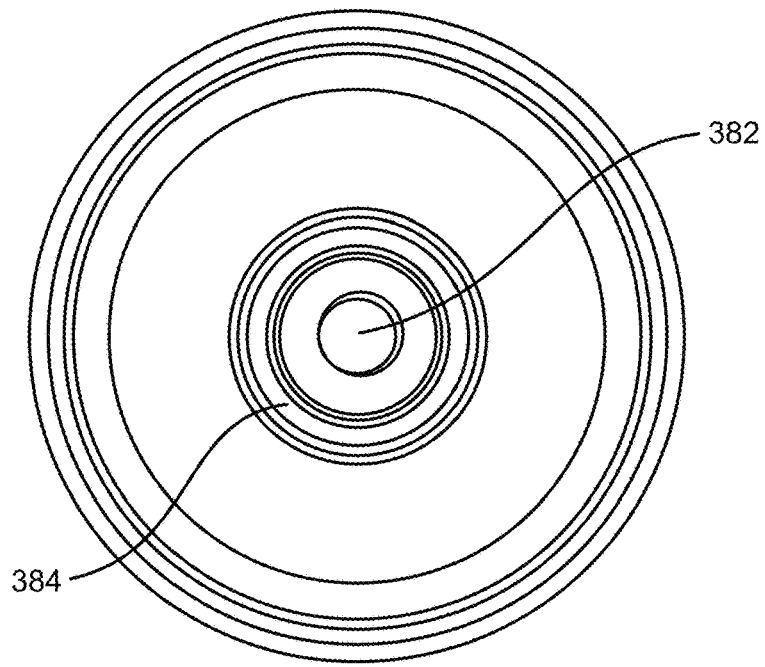
FIG. 40 is a top view of the glenosphere of FIG. 38, in accordance with an aspect of the present disclosure.
Figure 41:
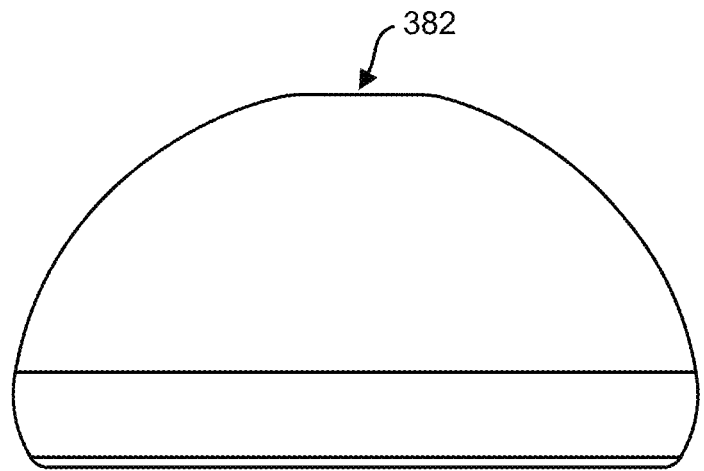
FIG. 41 is a side view of the glenosphere of FIG. 38, in accordance with an aspect of the present disclosure.
Figure 42:
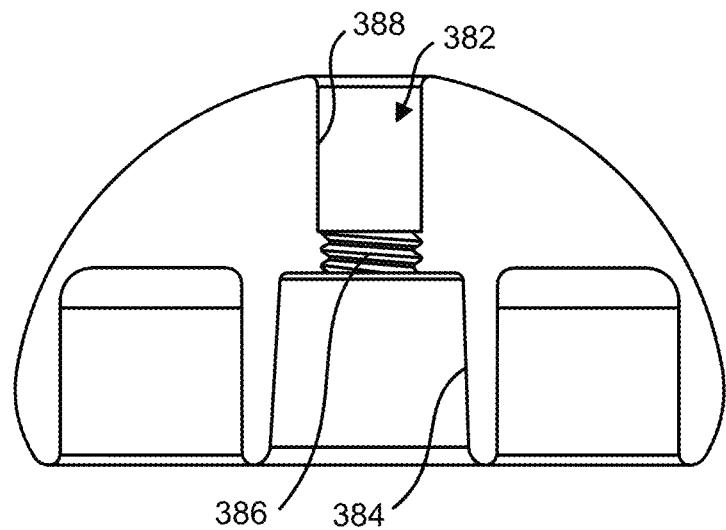
FIG. 42 is a cross-sectional side view of the glenosphere of FIG. 38, in accordance with an aspect of the present disclosure.

Referring now to FIGS. 35-37, a coupling member or modular taper 360. The modular taper 360 includes an exterior tapered cylindrical shape. The modular taper 360 further includes a distal exterior threaded portion 362 and a proximal recess 364 for engaging a torque device, such as, a screwdriver. The modular taper 360 also includes a central bore 366 disposed through the modular taper 360. As shown in FIGS. 21 and 22, the modular taper 360 threadedly connects within the central bore 316 of the baseplate 310.

Referring now to FIGS. 38-42, of the glenosphere 380 is shown. The glenosphere 380 includes a hemispherical shape and a central bore 382 having a distal tapered portion 384, a central threaded portion 386, and a proximal cylindrical portion 388. As illustrated in FIGS. 21 and 22, the glenosphere 380 is disposed atop the modular taper 360 such that the exterior of the modular taper 360 and the distal tapered portion 384 of the glenosphere bore 382 form a mechanical taper connection.

Referring now collectively to FIGS. 28-30, a post 390 is shown. The post 390 includes a cylindrical proximal head 392 having a diameter and a proximal recess 394 for engaging a torque device. The post 390 further includes a central portion 396 having a diameter smaller than the diameter of the post proximal head 392 and a distal portion 398 having a diameter smaller than the diameter of the post proximal head 392. The post 390 also includes an exterior thread portion 400 disposed along a portion of the post 390 between the central post portion 396 and the distal post portion 398. When assembled, as illustrated in FIGS. 21 and 22, the post 390 is disposed through the central bore 382 of the glenosphere 380, through the central bore 366 of the modular taper 360, and threadedly connected to the recess 336 of the central screw 330.

An implant 300 in accordance with the present disclosure offers several advantages over other known reverse glenoid devices. The baseplate 310 can accept a central locking screw 330 to provide compression, then is locked in place to rigidify the construct via a taper cap 360 that will accept the glenosphere 380. This construct can be pre-assembled to allow the surgeon to insert the entire locked construct 300 as one piece to streamline the process or simplify revision surgeries. The taper that can be added later and/or have built-in offset to allow eccentricity or have a longer taper option to build in lateralization.

The screw 330 has a post portion that essentially replaces the distal post of the baseplate, and transfers that geometry to the screw, allowing the post to be much smaller in diameter since a screw does not need to pass through it and ultimately conserves bone. Additionally, the screw 330 passes through the baseplate and provides compression via the screw portion as well as long term fixation via the proximal portion.

An exemplary method of using an orthopedic implant assembly 300 includes placing a baseplate 310 into the bone, inserting a central screw 330 through the baseplate 310 into the bone, inserting a peripheral compression screw 350 through a peripheral bore 322 of the baseplate 310 into the bone, and screwing a modular taper 360 into the central bore 316 of the baseplate 310. These steps may be performed during an open surgical procedure or pre-assembled prior to surgery.

Next, an exemplary method of using the implant 300 of the present disclosure includes placing a glenosphere 380 onto the modular taper 360 and inserting the post 390 through the glenosphere 380 and the taper 360 then threading the same into the central screw 330.

As may be recognized by those of ordinary skill in the art based on the teachings herein, numerous changes and modifications may be made to the above-described and other embodiments of the present disclosure without departing from the scope of the disclosure. The components of the implants, devices, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants, devices, and/or systems may include more or fewer components or features than the embodiments as described and illustrated herein. For example, the components and features of implants 100, 300 may be used interchangeably and in alternative combinations as would be modified or altered by one of skill in the art. Further, the steps of the surgical methods associated with the implants 100, 300 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An orthopedic implant assembly, comprising:
    a baseplate comprising:
        a cylindrical shape;
        an upper surface;
        a lower surface;
        a central bore disposed from the upper surface to the lower surface;
        a plurality of peripheral bores disposed around the central bore;
        a plurality of discrete arcuated keels extending from a bottom surface of the baseplate, the central bore having a proximal interior threaded section and a distal non-threaded section;
    a central screw having a central axis, a proximal non-threaded section having a cylindrical shape, and a distal threaded section, said central screw further comprising a proximal head portion, said proximal head portion having a surface area that increases in a direction opposite said distal threaded section, said central screw further comprising a recess having a proximal section for engaging a torque device, a central threaded portion, and a distal non-threaded portion, said recess disposed through said proximal head portion, said central screw slidingly disposed through said central bore of said baseplate, where a diameter of said proximal head portion is greater than a diameter of said non-threaded section of said central bore of said baseplate such that said central screw is captured by said baseplate central bore, said central screw suitable for threading into a bone;
    a peripheral compression screw disposed through one of said plurality of peripheral bores, said peripheral compression screw suitable for threading into a bone;
    a modular taper having a tapered cylindrical shape, a distal threaded portion and a proximal recess for engaging a torque device, and a central bore, said modular taper threadedly connected to said central bore of said baseplate, wherein the modular taper locks the central screw to the baseplate;
    a glenosphere having a hemispherical shape and a central bore having a distal tapered portion, a central threaded portion, and a proximal cylindrical portion, said glenosphere disposed atop said modular taper such that an exterior of said modular taper and the distal tapered portion of said glenosphere bore form a mechanical taper connection; and
    a post having a cylindrical proximal head having a diameter and a proximal recess for engaging a torque device, said post further comprising a central post portion having a diameter smaller than the diameter of said cylindrical proximal head, said post further having a distal post portion having a diameter smaller than the diameter of said cylindrical proximal head, said post further comprising an exterior threaded portion, said exterior threaded portion disposed along a portion of said post between said central post portion and said distal post portion, said post disposed through said central bore of said glenosphere and said central bore of said modular taper, said post further disposed into and threadedly connected to said recess of said central screw.

2. The orthopedic implant assembly of claim 1, wherein said proximal non-threaded section comprises a surface selected from the group consisting of porous, textured, indented, and sprayed.

3. An orthopedic implant assembly, comprising:
    a baseplate, said baseplate having a cylindrical shape, an upper surface, and a lower surface, said baseplate further comprising a central bore disposed from said upper surface to said lower surface, said baseplate further comprising a plurality of discrete arcuated keels extending from a bottom surface of said baseplate, said central bore having a proximal interior threaded section and a distal non-threaded section;
    a central screw, said central screw having a central axis, a proximal non-threaded section having a cylindrical shape, and a distal threaded section, said central screw further comprising a proximal head portion, said proximal head portion having a surface area that increases in a direction opposite said distal threaded section, said central screw further comprising a recess having a proximal section for engaging a torque device, a central threaded portion, and a distal non-threaded portion, said recess disposed through said proximal head portion, said central screw slidingly disposed through said central bore of said baseplate, wherein a diameter of said proximal head portion is greater than a diameter of said non-threaded section of said central bore of said baseplate such that said central screw is captured by said baseplate central bore, said central screw suitable for threading into a bone;
    a modular taper, said modular taper having a tapered cylindrical shape, a distal threaded portion and a proximal recess for engaging a torque device, and a central bore, said modular taper threadedly connected to said central bore of said baseplate;

a glenosphere, said glenosphere having a hemispherical shape and a central bore having a distal tapered portion, a central threaded portion, and a proximal cylindrical portion, said glenosphere disposed atop said modular taper such that an exterior of said modular taper and the distal tapered portion of said glenosphere bore form a mechanical taper connection; and a post, said post having a cylindrical post proximal head having a diameter and a proximal recess for engaging a torque device, said post further comprised a central post portion having a diameter smaller than the diameter of said post proximal head, said post further having a distal post portion having a diameter smaller than the diameter of said post proximal head, said post further comprising an exterior threaded portion, said exterior threaded portion disposed along a portion of said post between said central post portion and said distal post portion, said post disposed through said central bore of said glenosphere and said central bore of said modular taper, said post further disposed into and threadedly connected to said recess of said central screw.

4. The orthopedic implant assembly of claim 3, wherein said proximal non-threaded section of said central screw comprises a surface selected from the group consisting of porous, textured, indented, and sprayed.

5. An orthopedic implant assembly system, said implant assembly system comprising:
at least one baseplate having a cylindrical shape, an upper surface, and a lower surface, said baseplate further comprising a central bore disposed from said upper surface to said lower surface, and a plurality of peripheral bores disposed around said central bore; said baseplate further comprising a plurality of discrete arcuated keels extending from a bottom surface of said baseplate, said central bore having a proximal interior threaded section and a distal non-threaded section;
a plurality of central screws, each screw of said plurality of central screws having a central axis, a proximal non-threaded section having a cylindrical shape, and a distal threaded section, said central screws further comprising a proximal head portion, said proximal head portion having a surface area that increases in a direction opposite said distal threaded section, said central screws further comprising a recess having a proximal section for engaging a torque device, a central threaded portion, and a distal non-threaded portion, said recess disposed through said proximal head portion, said central screws slidingly disposed through said central bore of said baseplate, where a diameter of said proximal head portion is greater than a diameter of said non-threaded section of said central bore of said baseplate such that said central screws are captured by said baseplate central bore, said central screws suitable for threading into a bone;
at least one peripheral compression screw, said peripheral compression screw disposed through one of said plurality of peripheral bores, said peripheral compression screw suitable for threading into a bone;
at least one modular taper, said modular taper having a tapered cylindrical shape, a distal threaded portion and a proximal recess for engaging a torque device, and a central bore, said modular taper threadedly connected to said central bore of said baseplate;
a plurality of glenospheres, each glenosphere of said plurality of glenospheres having a hemispherical shape and a central bore having a distal tapered portion, a central threaded portion, and a proximal cylindrical portion, said glenospheres disposed atop said modular taper such that an exterior of said modular taper and the distal tapered portion of said glenospheres bore form a mechanical taper connection; and at least one post, said post having a cylindrical post proximal head having a diameter and a proximal recess for engaging a torque device, said post further comprised a central portion having a diameter smaller than the diameter of said post proximal head, said post further having a distal portion having a diameter smaller than the diameter of said post proximal head, said post further comprising an exterior threaded portion, said exterior threaded portion disposed along a portion of said post between said central portion and said distal portion, said post disposed through said central bore of said glenospheres and said central bore of said modular taper, said post further disposed into and threadedly connected to said recess of said central screws.

6. The orthopedic implant assembly system of claim 5, wherein each said screw of said plurality of central screws comprises a different threaded portion length.

7. The orthopedic implant assembly system of claim 5, wherein each said screw of said plurality of central screws comprises a different non-threaded portion length.

8. The orthopedic implant assembly system of claim 5, wherein said proximal non-threaded section of each central screw of said plurality of central screws comprises a surface selected from the group consisting of porous, textured, indented, and sprayed.

9. The orthopedic implant assembly system of claim 8, wherein each said screw of said plurality of central screws comprises a different threaded portion length.

10. The orthopedic implant assembly system of claim 8, wherein each said screw of said plurality of central screws comprises a different non-threaded portion length.

11. A method of using the orthopedic implant assembly of claim 1, said method comprising:
surgically exposing and resecting a desired bone;
inserting the baseplate into said bone;
inserting the central screw through said baseplate into said bone;
inserting the peripheral compression screw through one of said plurality of peripheral bores into said bone;
screwing the modular taper into said central bore of said baseplate;
placing the glenosphere onto said modular taper; and
inserting the post through said glenosphere and taper and threading the post into said recess of said central screw.

12. The method of claim 11, wherein the baseplate, the central screw and the modular taper are pre-assembled as a single unit and inserted into an implant as a single unit.

13. A method of using the orthopedic implant assembly of claim 3, said method comprising:
surgically exposing and resecting a desired bone;
inserting the baseplate into said bone;
inserting the central screw through said baseplate into said bone;
screwing the modular taper into said central bore of said baseplate;
placing the glenosphere onto said modular taper; and
inserting the post through said glenosphere and taper and threading the post into said recess of said central screw.

14. The method of claim 13, wherein the baseplate, the central screw, and the modular taper are pre-assembled as a single unit and inserted into an implant as a single unit.

15. The method of claim 13, wherein the baseplate further comprises a plurality of peripheral bores disposed around the central bore, and further comprising:

inserting a peripheral screw through a peripheral bore of the plurality of peripheral bores into the bone.

16. The method of claim 15, wherein the baseplate, the central screw, and the modular taper are pre-assembled as a single unit and inserted into an implant as a single unit.

17. A method of using the orthopedic implant assembly system of claim 5, said method comprising:

surgically exposing and resecting a desired bone;

selecting a baseplate from the at least one baseplate and inserting said baseplate into said bone;

selecting a central screw from the plurality of central screws and inserting said central screw through said baseplate into said bone;

selecting a peripheral screw from the at least one peripheral compression screw and inserting said peripheral screw through a peripheral bore of said plurality of peripheral bores into said bone;

selecting a modular taper from the at least one modular taper and screwing said modular taper into said central bore of said baseplate;

selecting a glenosphere from the plurality of glenospheres and placing said glenosphere onto said modular taper; and selecting a post from the at least one post and inserting said post through said glenosphere and taper and threading the post into said recess of said central screw.

18. The method of claim 17, wherein said baseplate, said central screw and said modular taper are pre-assembled as a single unit and inserted into an implant as a single unit.

\* \* \* \* \*